(12) United States Patent
Freitag et al.

(10) Patent No.: US 8,418,694 B2
(45) Date of Patent: *Apr. 16, 2013

(54) SYSTEMS, METHODS AND APPARATUS FOR RESPIRATORY SUPPORT OF A PATIENT

(75) Inventors: Lutz Freitag, Hemer (DE); Gregory Kapust, San Ramon, CA (US)

(73) Assignee: Breathe Technologies, Inc., Irvine, CA (US)

( * ) Notice: Subject to any disclaimer, the term of this patent is extended or adjusted under 35 U.S.C. 154(b) by 90 days.

This patent is subject to a terminal disclaimer.

(21) Appl. No.: 12/771,651

(22) Filed: Apr. 30, 2010

(65) Prior Publication Data

US 2010/0269834 A1    Oct. 28, 2010

Related U.S. Application Data

(63) Continuation of application No. 11/523,518, filed on Sep. 20, 2006, now abandoned, which is a continuation-in-part of application No. 10/771,803, filed on Feb. 4, 2004, now Pat. No. 7,487,778, and a continuation-in-part of application No. 10/567,746, filed as application No. PCT/DE2004/001646 on Jul. 23, 2004, now abandoned.

(60) Provisional application No. 60/718,318, filed on Sep. 20, 2005.

(30) Foreign Application Priority Data

Aug. 11, 2003  (DE) .............................. 20/40963-001

(51) Int. Cl.
*A61M 11/00* (2006.01)
(52) U.S. Cl.
USPC ................................ 128/207.14; 128/207.16

(58) Field of Classification Search ............. 128/200.26, 128/207.14, 207.15, 207.16, 207.24, 204.18, 128/204.23; 623/9; 604/99.01, 102.01, 103.01
See application file for complete search history.

(56) References Cited

U.S. PATENT DOCUMENTS

| 50,641 A | 10/1865 | Stone |
|---|---|---|
| 428,592 A | 5/1890 | Chapman |

(Continued)

FOREIGN PATENT DOCUMENTS

| DE | 19626924 | 1/1998 |
|---|---|---|
| DE | 29902267 U1 | 7/1999 |

(Continued)

OTHER PUBLICATIONS

In the U.S. Patent and Trademark Office, Supplemental Notice of Allowance dated in re: U.S. Appl. No. 10/771,803, dated Dec. 2, 2008, 2 pages.

(Continued)

*Primary Examiner* — Steven Douglas
(74) *Attorney, Agent, or Firm* — Stetina Brunda Garred & Brucker

(57) ABSTRACT

Spontaneous respiration is detected by sensors. An additional amount of oxygen is administered to the lungs via a jet gas current at the end of an inhalation procedure. Breathing volume, absorption of oxygen during inhalation, and clearance of carbon dioxide during exhalation are improved. If required, the exhalation procedure of the patient can be arrested or slowed by a countercurrent to avoid a collapse of the respiration paths. An apparatus including an oxygen pump can be connected to an oxygen source and includes a tracheal prosthesis that can be connected via a catheter. The respiration detections sensors are connected to a control unit for activating the oxygen pump. The tracheal prosthesis includes a tubular support body with a connection for the catheter, and the sensors are associated with the support body. The tracheal prosthesis and jet catheter are dimensioned so the patient can freely breathe and speak without restriction.

64 Claims, 14 Drawing Sheets

U.S. PATENT DOCUMENTS

| | | |
|---|---|---|
| 697,181 A | 4/1902 | Smith |
| 718,785 A | 1/1903 | McNary |
| 853,439 A | 5/1907 | Clark |
| 859,156 A | 7/1907 | Warnken |
| 909,002 A | 1/1909 | Lambert |
| 1,125,542 A | 1/1915 | Humphries |
| 1,129,619 A | 2/1915 | Zapf |
| 1,331,297 A | 2/1920 | Walker |
| 2,178,800 A | 11/1939 | Lombard |
| 2,259,817 A | 10/1941 | Hawkins |
| 2,552,595 A | 5/1951 | Seeler |
| 2,663,297 A | 12/1953 | Turnberg |
| 2,693,800 A | 11/1954 | Caldwell |
| 2,735,432 A | 2/1956 | Hudson |
| 2,792,000 A | 5/1957 | Richardson |
| 2,843,122 A | 7/1958 | Hudson |
| 2,859,748 A | 11/1958 | Hudson |
| 2,931,358 A | 4/1960 | Sheridan |
| 2,947,938 A | 8/1960 | Bennett |
| 3,172,407 A | 3/1965 | Von Pechmann |
| 3,267,935 A | 8/1966 | Andreasen et al. |
| 3,319,627 A | 5/1967 | Windsor |
| 3,357,424 A | 12/1967 | Schreiber |
| 3,357,427 A | 12/1967 | Wittke et al. |
| 3,357,428 A | 12/1967 | Carlson |
| 3,437,274 A | 4/1969 | Apri |
| 3,460,533 A | 8/1969 | Riú Plá |
| 3,493,703 A | 2/1970 | Finan |
| 3,513,844 A | 5/1970 | Smith |
| 3,610,247 A | 10/1971 | Jackson |
| 3,625,206 A | 12/1971 | Charnley |
| 3,625,207 A | 12/1971 | Agnew |
| 3,631,438 A | 12/1971 | Lewin |
| 3,643,660 A | 2/1972 | Hudson et al. |
| 3,657,740 A | 4/1972 | Cialone |
| 3,682,171 A | 8/1972 | Dali et al. |
| 3,721,233 A | 3/1973 | Montgomery et al. |
| 3,726,275 A | 4/1973 | Jackson et al. |
| 3,727,606 A | 4/1973 | Sielaff |
| 3,733,008 A | 5/1973 | Churchill et al. |
| 3,741,208 A | 6/1973 | Jonsson et al. |
| 3,754,552 A | 8/1973 | King |
| 3,794,026 A | 2/1974 | Jacobs |
| 3,794,072 A | 2/1974 | Diedrich et al. |
| 3,802,431 A | 4/1974 | Farr |
| 3,831,596 A | 8/1974 | Cavallo |
| 3,881,480 A | 5/1975 | Lafourcade |
| 3,896,800 A | 7/1975 | Cibulka |
| 3,903,881 A | 9/1975 | Weigl |
| 3,905,362 A | 9/1975 | Eyrick et al. |
| 3,949,749 A | 4/1976 | Stewart |
| 3,951,143 A | 4/1976 | Kitrilakis et al. |
| 3,961,627 A | 6/1976 | Ernst et al. |
| 3,972,327 A | 8/1976 | Ernst et al. |
| 3,985,131 A | 10/1976 | Buck et al. |
| 3,991,790 A | 11/1976 | Russell |
| 4,003,377 A | 1/1977 | Dahl |
| 4,036,253 A | 7/1977 | Fegan et al. |
| 4,054,133 A | 10/1977 | Myers |
| 4,067,328 A | 1/1978 | Manley |
| 4,106,505 A | 8/1978 | Salter et al. |
| 4,146,885 A | 3/1979 | Lawson, Jr. |
| 4,206,754 A | 6/1980 | Cox et al. |
| 4,211,086 A | 7/1980 | Leonard et al. |
| 4,216,769 A | 8/1980 | Grimes |
| 4,231,363 A | 11/1980 | Grimes |
| 4,231,365 A | 11/1980 | Scarberry |
| 4,256,101 A | 3/1981 | Ellestad |
| 4,261,355 A | 4/1981 | Glazener |
| 4,263,908 A | 4/1981 | Mizerak |
| 4,265,237 A | 5/1981 | Schwanbom et al. |
| 4,266,540 A | 5/1981 | Panzik et al. |
| 4,273,124 A | 6/1981 | Zimmerman |
| 4,274,162 A | 6/1981 | Joy et al. |
| 4,278,082 A | 7/1981 | Blackmer |
| 4,282,869 A | 8/1981 | Zidulka |
| 4,306,567 A | 12/1981 | Krasner |
| 4,323,064 A | 4/1982 | Hoenig et al. |
| 4,354,488 A | 10/1982 | Bartos |
| 4,365,636 A | 12/1982 | Barker |
| 4,367,735 A | 1/1983 | Dali |
| 4,377,162 A | 3/1983 | Staver |
| 4,393,869 A | 7/1983 | Boyarsky et al. |
| 4,406,283 A | 9/1983 | Bir |
| 4,411,267 A | 10/1983 | Heyman |
| 4,413,514 A | 11/1983 | Bowman |
| 4,421,113 A | 12/1983 | Gedeon et al. |
| 4,422,456 A | 12/1983 | Tiep |
| 4,449,523 A | 5/1984 | Szachowicz et al. |
| 4,454,880 A | 6/1984 | Muto et al. |
| 4,462,398 A | 7/1984 | Durkan et al. |
| 4,469,097 A | 9/1984 | Kelman |
| 4,481,944 A | 11/1984 | Bunnell |
| 4,488,548 A | 12/1984 | Agdanowski |
| 4,495,946 A | 1/1985 | Lemer |
| 4,506,666 A | 3/1985 | Durkan |
| 4,506,667 A | 3/1985 | Ansite |
| 4,519,387 A | 5/1985 | Durkan et al. |
| 4,520,812 A | 6/1985 | Freitag et al. |
| 4,527,557 A | 7/1985 | DeVries et al. |
| 4,535,766 A | 8/1985 | Baum |
| 4,537,188 A | 8/1985 | Phuc |
| 4,539,984 A | 9/1985 | Kiszel et al. |
| 4,548,590 A | 10/1985 | Green |
| 4,559,940 A | 12/1985 | McGinnis |
| 4,570,631 A | 2/1986 | Durkan |
| 4,571,741 A | 2/1986 | Guillaumot |
| 4,584,996 A | 4/1986 | Blum |
| 4,590,951 A | 5/1986 | O'Connor |
| 4,592,349 A | 6/1986 | Bird |
| 4,621,632 A | 11/1986 | Bartels et al. |
| 4,630,606 A | 12/1986 | Weerda et al. |
| 4,630,614 A | 12/1986 | Atlas |
| 4,644,947 A | 2/1987 | Whitwam et al. |
| 4,648,395 A | 3/1987 | Sato et al. |
| 4,648,398 A | 3/1987 | Agdanowski et al. |
| 4,658,832 A | 4/1987 | Brugnoli |
| 4,660,555 A | 4/1987 | Payton |
| 4,682,591 A | 7/1987 | Jones |
| 4,684,398 A | 8/1987 | Dunbar et al. |
| 4,686,974 A | 8/1987 | Sato et al. |
| 4,686,975 A | 8/1987 | Naimon et al. |
| 4,688,961 A | 8/1987 | Shioda et al. |
| 4,705,034 A | 11/1987 | Perkins |
| 4,744,356 A | 5/1988 | Greenwood |
| 4,747,403 A | 5/1988 | Gluck et al. |
| 4,753,233 A | 6/1988 | Grimes |
| 4,773,411 A | 9/1988 | Downs |
| 4,776,333 A | 10/1988 | Miyamae |
| 4,782,832 A | 11/1988 | Trimble et al. |
| 4,784,130 A | 11/1988 | Kenyon et al. |
| 4,803,981 A | 2/1989 | Vickery |
| 4,807,616 A | 2/1989 | Adahan |
| 4,807,617 A | 2/1989 | Nesti |
| 4,808,160 A | 2/1989 | Timmons et al. |
| 4,813,431 A | 3/1989 | Brown |
| 4,817,897 A | 4/1989 | Kreusel |
| 4,818,320 A | 4/1989 | Weichselbaum |
| 4,823,788 A | 4/1989 | Smith et al. |
| 4,825,859 A | 5/1989 | Lambert |
| 4,827,922 A | 5/1989 | Champain et al. |
| 4,832,014 A | 5/1989 | Perkins |
| 4,838,255 A | 6/1989 | Lambert |
| 4,841,953 A | 6/1989 | Dodrill |
| 4,848,333 A | 7/1989 | Waite |
| 4,850,350 A | 7/1989 | Jackson |
| 4,865,586 A | 9/1989 | Hedberg |
| 4,869,718 A | 9/1989 | Brader |
| 4,899,740 A | 2/1990 | Napolitano |
| 4,905,688 A | 3/1990 | Vicenzi et al. |
| 4,915,103 A | 4/1990 | Visveshwara et al. |
| 4,915,105 A | 4/1990 | Lee |
| 4,919,128 A | 4/1990 | Kopala et al. |
| 4,919,132 A | 4/1990 | Miser |
| 4,938,212 A | 7/1990 | Snook et al. |
| 4,944,310 A | 7/1990 | Sullivan |
| 4,967,743 A | 11/1990 | Lambert |

| | | |
|---|---|---|
| 4,971,049 A | 11/1990 | Rotariu et al. |
| 4,982,735 A | 1/1991 | Yagata et al. |
| 4,986,269 A | 1/1991 | Hakkinen |
| 4,989,599 A | 2/1991 | Carter |
| 4,990,157 A | 2/1991 | Roberts et al. |
| 5,000,175 A | 3/1991 | Pue |
| 5,002,050 A | 3/1991 | McGinnis |
| 5,005,570 A | 4/1991 | Perkins |
| 5,018,519 A | 5/1991 | Brown |
| 5,022,394 A | 6/1991 | Chmielinski |
| 5,024,219 A | 6/1991 | Dietz |
| 5,025,805 A | 6/1991 | Nutter |
| 5,038,771 A | 8/1991 | Dietz |
| 5,042,478 A | 8/1991 | Kopala et al. |
| 5,046,491 A | 9/1991 | Derrick |
| 5,046,492 A | 9/1991 | Stackhouse et al. |
| 5,048,515 A | 9/1991 | Sanso |
| 5,048,516 A | 9/1991 | Soderberg |
| 5,052,400 A | 10/1991 | Dietz |
| 5,054,484 A | 10/1991 | Hebeler, Jr. |
| 5,058,580 A | 10/1991 | Hazard |
| 5,074,299 A | 12/1991 | Dietz |
| 5,076,267 A | 12/1991 | Pasternack |
| 5,090,408 A | 2/1992 | Spofford et al. |
| 5,097,827 A | 3/1992 | Izumi |
| 5,099,836 A | 3/1992 | Rowland et al. |
| 5,099,837 A | 3/1992 | Russel, Sr. et al. |
| 5,101,820 A | 4/1992 | Christopher |
| 5,103,815 A | 4/1992 | Siegel et al. |
| 5,105,807 A | 4/1992 | Kahn et al. |
| 5,107,830 A | 4/1992 | Younes |
| 5,107,831 A | 4/1992 | Halpern et al. |
| 5,113,857 A | 5/1992 | Dickerman et al. |
| 5,117,818 A | 6/1992 | Palfy |
| 5,117,819 A | 6/1992 | Servidio et al. |
| 5,127,400 A | 7/1992 | DeVries et al. |
| 5,134,995 A | 8/1992 | Gruenke et al. |
| 5,134,996 A | 8/1992 | Bell |
| 5,140,045 A | 8/1992 | Askanazi et al. |
| 5,148,802 A | 9/1992 | Sanders et al. |
| 5,161,525 A | 11/1992 | Kimm et al. |
| 5,165,397 A | 11/1992 | Arp |
| 5,181,509 A | 1/1993 | Spofford et al. |
| 5,184,610 A | 2/1993 | Marten et al. |
| 5,186,167 A | 2/1993 | Kolobow |
| 5,193,532 A | 3/1993 | Moa et al. |
| 5,193,533 A | 3/1993 | Body et al. |
| 5,199,424 A | 4/1993 | Sullivan et al. |
| 5,211,170 A | 5/1993 | Press |
| 5,217,008 A | 6/1993 | Lindholm |
| 5,233,978 A | 8/1993 | Callaway |
| 5,233,979 A | 8/1993 | Strickland |
| 5,239,994 A | 8/1993 | Atkins |
| 5,239,995 A | 8/1993 | Estes et al. |
| 5,243,972 A | 9/1993 | Huang |
| 5,245,995 A | 9/1993 | Sullivan et al. |
| 5,255,675 A | 10/1993 | Kolobow |
| 5,258,027 A | 11/1993 | Berghaus |
| 5,269,296 A | 12/1993 | Landis |
| 5,271,388 A | 12/1993 | Whitwam et al. |
| 5,271,391 A | 12/1993 | Graves |
| 5,275,159 A | 1/1994 | Griebel |
| 5,279,288 A | 1/1994 | Christopher |
| 5,287,852 A | 2/1994 | Arkinstall |
| 5,303,698 A | 4/1994 | Tobia et al. |
| 5,303,700 A | 4/1994 | Weismann et al. |
| 5,318,019 A | 6/1994 | Celaya |
| 5,331,995 A | 7/1994 | Westfall et al. |
| 5,335,656 A | 8/1994 | Bowe et al. |
| 5,339,809 A | 8/1994 | Beck, Jr. et al. |
| 5,349,946 A | 9/1994 | McComb |
| 5,368,017 A | 11/1994 | Sorenson et al. |
| 5,370,112 A | 12/1994 | Perkins |
| 5,373,842 A | 12/1994 | Olsson et al. |
| 5,375,593 A | 12/1994 | Press |
| 5,388,575 A | 2/1995 | Taube |
| 5,394,870 A | 3/1995 | Johansson |
| 5,398,676 A | 3/1995 | Press et al. |
| 5,398,682 A | 3/1995 | Lynn |
| 5,400,778 A | 3/1995 | Jonson et al. |
| 5,419,314 A | 5/1995 | Christopher |
| 5,438,979 A | 8/1995 | Johnson, Jr. et al. |
| 5,438,980 A | 8/1995 | Phillips |
| 5,443,075 A | 8/1995 | Holscher |
| 5,460,174 A | 10/1995 | Chang |
| 5,460,613 A | 10/1995 | Ulrich et al. |
| 5,474,062 A | 12/1995 | DeVires et al. |
| 5,477,852 A | 12/1995 | Landis et al. |
| 5,485,850 A | 1/1996 | Dietz |
| 5,490,502 A | 2/1996 | Rapoport et al. |
| 5,503,146 A | 4/1996 | Froehlich et al. |
| 5,503,497 A | 4/1996 | Dudley et al. |
| 5,507,282 A | 4/1996 | Younes |
| 5,509,409 A | 4/1996 | Weatherholt |
| 5,513,628 A | 5/1996 | Coles et al. |
| 5,513,631 A | 5/1996 | McWilliams |
| 5,513,635 A | 5/1996 | Bedi |
| 5,522,382 A | 6/1996 | Sullivan et al. |
| 5,526,806 A | 6/1996 | Sansoni |
| 5,529,060 A | 6/1996 | Salmon et al. |
| 5,533,506 A | 7/1996 | Wood |
| 5,535,738 A | 7/1996 | Estes et al. |
| 5,537,997 A | 7/1996 | Mechlenburg et al. |
| 5,538,002 A | 7/1996 | Boussignac et al. |
| 5,542,415 A | 8/1996 | Brody |
| 5,546,935 A | 8/1996 | Champeau |
| 5,549,106 A | 8/1996 | Gruenke et al. |
| 5,551,419 A | 9/1996 | Froehlich et al. |
| 5,558,086 A | 9/1996 | Smith et al. |
| 5,564,416 A | 10/1996 | Jones |
| 5,575,282 A | 11/1996 | Knoch et al. |
| 5,582,164 A | 12/1996 | Sanders |
| 5,593,143 A | 1/1997 | Ferrarin |
| 5,595,174 A | 1/1997 | Gwaltney |
| 5,598,837 A | 2/1997 | Sirianne, Jr. et al. |
| 5,598,840 A | 2/1997 | Iund et al. |
| 5,603,315 A | 2/1997 | Sasso, Jr. |
| 5,605,148 A | 2/1997 | Jones |
| 5,626,131 A | 5/1997 | Chua et al. |
| 5,632,269 A | 5/1997 | Zdrojkowski |
| 5,636,630 A | 6/1997 | Miller et al. |
| 5,645,053 A | 7/1997 | Remmers et al. |
| 5,645,054 A | 7/1997 | Cotner et al. |
| 5,647,351 A | 7/1997 | Weismann et al. |
| 5,669,377 A | 9/1997 | Fenn |
| 5,669,380 A | 9/1997 | Garry et al. |
| 5,676,132 A | 10/1997 | Tillotson et al. |
| 5,676,135 A | 10/1997 | McClean |
| 5,682,878 A | 11/1997 | Ogden |
| 5,682,881 A | 11/1997 | Winthrop et al. |
| 5,687,713 A | 11/1997 | Bahr et al. |
| 5,687,714 A | 11/1997 | Kolobow et al. |
| 5,687,715 A | 11/1997 | Landis et al. |
| 5,690,097 A | 11/1997 | Howard et al. |
| 5,692,497 A | 12/1997 | Schnitzer et al. |
| 5,697,364 A | 12/1997 | Chua et al. |
| 5,704,345 A | 1/1998 | Berthon-Jones |
| 5,711,296 A | 1/1998 | Kolobow |
| 5,715,812 A | 2/1998 | Deighan et al. |
| 5,715,815 A | 2/1998 | Lorenzen et al. |
| 5,720,278 A | 2/1998 | Lachmann et al. |
| 5,735,268 A | 4/1998 | Chua et al. |
| 5,735,272 A | 4/1998 | Dillon et al. |
| 5,740,796 A | 4/1998 | Skog |
| 5,752,511 A | 5/1998 | Simmons et al. |
| 5,762,638 A | 6/1998 | Shikani et al. |
| 5,791,337 A | 8/1998 | Coles et al. |
| 5,819,723 A | 10/1998 | Joseph |
| 5,826,579 A | 10/1998 | Remmers et al. |
| 5,845,636 A | 12/1998 | Gruenke et al. |
| 5,865,173 A | 2/1999 | Froehlich |
| 5,865,174 A | 2/1999 | Kloeppel |
| 5,881,723 A | 3/1999 | Wallace et al. |
| 5,904,648 A | 5/1999 | Arndt et al. |
| 5,906,204 A | 5/1999 | Beran et al. |
| 5,911,756 A | 6/1999 | Debry |
| 5,915,379 A | 6/1999 | Wallace et al. |
| 5,915,381 A | 6/1999 | Nord |

| | | | |
|---|---|---|---|
| 5,918,597 A | 7/1999 | Jones et al. | |
| 5,921,238 A | 7/1999 | Bourdon | |
| 5,921,942 A | 7/1999 | Remmers et al. | |
| 5,921,952 A | 7/1999 | Desmond, III et al. | |
| 5,927,276 A | 7/1999 | Rodriguez | |
| 5,928,189 A | 7/1999 | Phillips et al. | |
| 5,931,160 A | 8/1999 | Gilmore et al. | |
| 5,931,162 A | 8/1999 | Christian | |
| 5,937,853 A | 8/1999 | Strom | |
| 5,937,855 A | 8/1999 | Zdrojkowski et al. | |
| 5,938,118 A | 8/1999 | Cooper | |
| 5,954,050 A | 9/1999 | Christopher | |
| 5,957,136 A | 9/1999 | Magidson et al. | |
| 5,964,223 A | 10/1999 | Baran | |
| 5,975,077 A | 11/1999 | Hofstetter et al. | |
| 5,975,081 A | 11/1999 | Hood et al. | |
| 5,979,440 A | 11/1999 | Honkonen et al. | |
| 5,989,193 A | 11/1999 | Sullivan | |
| 6,000,396 A | 12/1999 | Melker et al. | |
| 6,019,101 A | 2/2000 | Cotner et al. | |
| 6,039,696 A | 3/2000 | Bell | |
| 6,050,260 A | 4/2000 | Daniell et al. | |
| 6,076,519 A | 6/2000 | Johnson | |
| 6,085,747 A | 7/2000 | Axe et al. | |
| 6,091,973 A | 7/2000 | Colla et al. | |
| 6,093,169 A | 7/2000 | Cardoso | |
| 6,105,575 A | 8/2000 | Estes et al. | |
| 6,109,264 A | 8/2000 | Sauer | |
| 6,112,746 A | 9/2000 | Kwok et al. | |
| 6,119,694 A | 9/2000 | Correa et al. | |
| 6,120,460 A | 9/2000 | Abreu | |
| 6,123,668 A | 9/2000 | Abreu | |
| 6,131,571 A | 10/2000 | Lampotang et al. | |
| 6,135,970 A | 10/2000 | Kadhiresan et al. | |
| 6,152,132 A | 11/2000 | Psaros | |
| 6,152,134 A | 11/2000 | Webber et al. | |
| 6,158,432 A | 12/2000 | Biondi et al. | |
| 6,192,883 B1 | 2/2001 | Miller, Jr. | |
| 6,203,502 B1 | 3/2001 | Hilgendorf et al. | |
| 6,213,119 B1 | 4/2001 | Brydon et al. | |
| 6,213,955 B1 | 4/2001 | Karakasoglu et al. | |
| 6,220,244 B1 | 4/2001 | McLaughlin | |
| 6,224,560 B1 | 5/2001 | Gazula et al. | |
| 6,227,200 B1 | 5/2001 | Crump et al. | |
| 6,247,470 B1 | 6/2001 | Ketchedjian | |
| 6,269,811 B1 | 8/2001 | Duff et al. | |
| 6,269,812 B1 | 8/2001 | Wallace et al. | |
| 6,273,859 B1 | 8/2001 | Remmers et al. | |
| 6,286,508 B1 | 9/2001 | Remmers et al. | |
| D449,376 S | 10/2001 | McDonald et al. | |
| D449,883 S | 10/2001 | McDonald et al. | |
| 6,298,850 B1 | 10/2001 | Argraves | |
| 6,305,374 B1 | 10/2001 | Zdrojkowski et al. | |
| 6,314,957 B1 | 11/2001 | Boissin et al. | |
| 6,315,739 B1 | 11/2001 | Merilainen et al. | |
| D451,598 S | 12/2001 | McDonald et al. | |
| 6,328,038 B1 | 12/2001 | Kessler et al. | |
| 6,328,753 B1 | 12/2001 | Zammit | |
| 6,332,463 B1 | 12/2001 | Farrugia et al. | |
| 6,345,619 B1 | 2/2002 | Finn | |
| 6,357,438 B1 | 3/2002 | Hansen | |
| 6,357,440 B1 | 3/2002 | Hansen et al. | |
| 6,360,741 B2 | 3/2002 | Truschel | |
| 6,360,745 B1 | 3/2002 | Wallace et al. | |
| 6,363,933 B1 | 4/2002 | Berthon-Jones | |
| 6,367,474 B1 | 4/2002 | Berthon-Jones et al. | |
| 6,369,838 B1 | 4/2002 | Wallace et al. | |
| 6,371,114 B1 | 4/2002 | Schmidt et al. | |
| 6,378,520 B1 | 4/2002 | Davenport | |
| 6,390,091 B1 | 5/2002 | Banner et al. | |
| 6,394,088 B1 | 5/2002 | Frye et al. | |
| 6,398,739 B1 | 6/2002 | Sullivan et al. | |
| 6,418,928 B1 | 7/2002 | Bordewick et al. | |
| 6,422,240 B1 | 7/2002 | Levitsky et al. | |
| 6,423,001 B1 | 7/2002 | Abreu | |
| 6,427,690 B1 | 8/2002 | McCombs et al. | |
| 6,431,172 B1 | 8/2002 | Bordewick | |
| 6,439,228 B1 | 8/2002 | Hete et al. | |
| 6,439,229 B1 | 8/2002 | Du et al. | |
| 6,439,234 B1 | 8/2002 | Curti et al. |
| 6,439,235 B1 | 8/2002 | Larquet et al. |
| 6,450,164 B1 | 9/2002 | Banner et al. |
| 6,450,166 B1 | 9/2002 | McDonald et al. |
| 6,457,472 B1 | 10/2002 | Schwartz et al. |
| 6,467,477 B1 | 10/2002 | Frank et al. |
| 6,478,026 B1 | 11/2002 | Wood |
| 6,494,202 B2 | 12/2002 | Farmer |
| 6,494,206 B1 | 12/2002 | Bergamaschi et al. |
| 6,505,623 B1 | 1/2003 | Hansen |
| 6,505,624 B1 | 1/2003 | Campbell, Sr. |
| 6,516,801 B2 | 2/2003 | Boussignac |
| 6,520,176 B1 | 2/2003 | Dubois et al. |
| 6,520,183 B2 | 2/2003 | Amar |
| 6,530,373 B1 | 3/2003 | Patron et al. |
| 6,532,958 B1 | 3/2003 | Buan et al. |
| 6,532,960 B1 | 3/2003 | Yurko |
| 6,536,432 B2 | 3/2003 | Truschel |
| 6,536,436 B1 | 3/2003 | McGlothen |
| 6,550,478 B2 | 4/2003 | Remmers et al. |
| 6,553,992 B1 | 4/2003 | Berthon-Jones et al. |
| 6,561,188 B1 | 5/2003 | Ellis |
| 6,561,193 B1 | 5/2003 | Noble |
| 6,564,797 B1 | 5/2003 | Mechlenburg et al. |
| 6,564,800 B1 | 5/2003 | Olivares |
| 6,568,391 B1 | 5/2003 | Tatarek et al. |
| 6,571,794 B1 | 6/2003 | Hansen |
| 6,571,796 B2 | 6/2003 | Banner et al. |
| 6,571,798 B1 | 6/2003 | Thornton |
| 6,575,159 B1 | 6/2003 | Frye et al. |
| 6,575,944 B1 | 6/2003 | McNary et al. |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,591,834 B1 | 7/2003 | Colla et al. |
| 6,591,835 B1 | 7/2003 | Blanch |
| 6,595,207 B1 | 7/2003 | McDonald et al. |
| 6,595,215 B2 | 7/2003 | Wood |
| 6,609,517 B1 | 8/2003 | Estes et al. |
| 6,622,726 B1 | 9/2003 | Du |
| 6,626,174 B1 | 9/2003 | Genger et al. |
| 6,626,175 B2 | 9/2003 | Jafari et al. |
| 6,629,525 B2 | 10/2003 | Hill et al. |
| 6,629,527 B1 | 10/2003 | Estes et al. |
| 6,629,529 B2 | 10/2003 | Arnott |
| 6,631,919 B1 | 10/2003 | West et al. |
| 6,634,356 B1 | 10/2003 | O'Dea et al. |
| 6,635,021 B1 | 10/2003 | Sullivan et al. |
| 6,640,806 B2 | 11/2003 | Yurko |
| 6,644,305 B2 | 11/2003 | MacRae et al. |
| 6,644,311 B1 | 11/2003 | Truitt et al. |
| 6,644,315 B2 | 11/2003 | Ziaee |
| 6,651,653 B1 | 11/2003 | Honkonen et al. |
| 6,651,656 B2 | 11/2003 | Demers et al. |
| 6,651,658 B1 | 11/2003 | Hill et al. |
| 6,655,382 B1 | 12/2003 | Kolobow |
| 6,655,385 B1 | 12/2003 | Curti et al. |
| 6,666,208 B1 | 12/2003 | Schumacher et al. |
| 6,668,828 B1 | 12/2003 | Figley et al. |
| 6,668,829 B2 | 12/2003 | Biondi et al. |
| 6,669,712 B1 | 12/2003 | Cardoso |
| 6,675,796 B2 | 1/2004 | McDonald |
| 6,675,801 B2 | 1/2004 | Wallace et al. |
| 6,679,265 B2 | 1/2004 | Strickland et al. |
| 6,681,764 B1 | 1/2004 | Honkonen et al. |
| 6,684,883 B1 | 2/2004 | Burns |
| 6,691,702 B2 | 2/2004 | Appel et al. |
| 6,691,707 B1 | 2/2004 | Gunaratnam et al. |
| 6,694,973 B1 | 2/2004 | Dunhao et al. |
| 6,694,978 B1 | 2/2004 | Bennarsten |
| 6,698,423 B1 | 3/2004 | Honkonen et al. |
| 6,705,314 B1 | 3/2004 | O'Dea |
| 6,705,315 B2 | 3/2004 | Sullivan et al. |
| 6,722,360 B2 | 4/2004 | Doshi |
| 6,722,362 B2 | 4/2004 | Hete et al. |
| 6,742,517 B1 | 6/2004 | Frye et al. |
| 6,745,768 B2 | 6/2004 | Colla et al. |
| 6,752,150 B1 | 6/2004 | Remmers et al. |
| 6,752,151 B2 | 6/2004 | Hill |

| Patent No. | Date | Inventor |
|---|---|---|
| 6,752,152 B2 | 6/2004 | Gale et al. |
| 6,755,193 B2 | 6/2004 | Berthon-Jones et al. |
| 6,758,217 B1 | 7/2004 | Younes |
| 6,761,172 B2 | 7/2004 | Boussignac et al. |
| 6,763,832 B1 | 7/2004 | Kirsch et al. |
| 6,769,432 B1 | 8/2004 | Keifer |
| 6,776,162 B2 | 8/2004 | Wood |
| 6,776,163 B2 | 8/2004 | Dougill et al. |
| 6,789,539 B2 | 9/2004 | Martinez |
| 6,796,305 B1 | 9/2004 | Banner et al. |
| 6,799,575 B1 | 10/2004 | Carter |
| 6,805,126 B2 | 10/2004 | Dutkiewicz |
| 6,807,966 B2 | 10/2004 | Wright |
| 6,807,967 B2 | 10/2004 | Wood |
| 6,810,876 B2 | 11/2004 | Berthon-Jones |
| 6,814,073 B2 | 11/2004 | Wickham |
| 6,814,077 B1 | 11/2004 | Eistert |
| 6,823,866 B2 | 11/2004 | Jafari et al. |
| 6,827,340 B2 | 12/2004 | Austin et al. |
| 6,837,238 B2 | 1/2005 | McDonald |
| 6,840,240 B1 | 1/2005 | Berthon-Jones et al. |
| 6,843,247 B2 | 1/2005 | Frye et al. |
| 6,848,446 B2 | 2/2005 | Noble |
| 6,854,462 B2 | 2/2005 | Berthon-Jones et al. |
| 6,863,069 B2 | 3/2005 | Wood |
| 6,866,041 B2 | 3/2005 | Hardy, Jr. et al. |
| 6,877,511 B2 | 4/2005 | DeVries et al. |
| 6,880,556 B2 | 4/2005 | Uchiyama et al. |
| 6,910,480 B1 | 6/2005 | Berthon-Jones |
| 6,910,482 B2 | 6/2005 | Bliss et al. |
| 6,910,510 B2 | 6/2005 | Gale et al. |
| 6,913,601 B2 | 7/2005 | St. Goar et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,938,620 B1 | 9/2005 | Payne, Jr. |
| 6,941,950 B2 | 9/2005 | Wilson et al. |
| 6,948,497 B2 | 9/2005 | Zdrojkowski et al. |
| 6,951,217 B2 | 10/2005 | Berthon-Jones |
| 6,971,382 B1 | 12/2005 | Corso |
| 6,986,353 B2 | 1/2006 | Wright |
| 6,994,089 B2 | 2/2006 | Wood |
| 6,997,177 B2 | 2/2006 | Wood |
| 6,997,881 B2 | 2/2006 | Green et al. |
| 7,000,612 B2 | 2/2006 | Jafari et al. |
| 7,004,170 B1 | 2/2006 | Gillstrom |
| 7,007,692 B2 | 3/2006 | Aylsworth et al. |
| 7,011,091 B2 | 3/2006 | Hill et al. |
| 7,013,892 B2 | 3/2006 | Estes et al. |
| 7,013,898 B2 | 3/2006 | Rashad et al. |
| 7,017,574 B2 | 3/2006 | Biondi et al. |
| 7,017,575 B2 | 3/2006 | Yagi et al. |
| 7,024,945 B2 | 4/2006 | Wallace |
| 7,036,504 B2 | 5/2006 | Wallace et al. |
| 7,044,129 B1 | 5/2006 | Truschel et al. |
| 7,047,969 B2 | 5/2006 | Noble |
| 7,047,974 B2 | 5/2006 | Strickland et al. |
| 7,051,735 B2 | 5/2006 | Mechlenburg et al. |
| 7,055,522 B2 | 6/2006 | Berthon-Jones |
| 7,059,328 B2 | 6/2006 | Wood |
| 7,066,173 B2 | 6/2006 | Banner et al. |
| 7,066,178 B2 | 6/2006 | Gunaratnam et al. |
| 7,077,132 B2 | 7/2006 | Berthon-Jones |
| 7,077,133 B2 | 7/2006 | Yagi et al. |
| 7,080,645 B2 | 7/2006 | Genger et al. |
| 7,080,646 B2 | 7/2006 | Wiesmann et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,121,277 B2 | 10/2006 | Strom |
| 7,128,578 B2 | 10/2006 | Lampotang et al. |
| 7,152,598 B2 | 12/2006 | Morris et al. |
| 7,152,604 B2 | 12/2006 | Hickle et al. |
| 7,156,090 B2 | 1/2007 | Nomori |
| 7,156,097 B2 | 1/2007 | Cardoso |
| 7,162,296 B2 | 1/2007 | Leonhardt et al. |
| 7,168,429 B2 | 1/2007 | Matthews et al. |
| 7,188,621 B2 | 3/2007 | DeVries et al. |
| 7,188,624 B2 | 3/2007 | Wood |
| 7,195,016 B2 | 3/2007 | Loyd et al. |
| 7,195,018 B1 | 3/2007 | Goldstein |
| 7,201,169 B2 | 4/2007 | Wilkie et al. |
| 7,201,269 B2 | 4/2007 | Buscher et al. |
| D542,912 S | 5/2007 | Gunaratnam et al. |
| 7,222,623 B2 | 5/2007 | DeVries et al. |
| 7,225,811 B2 | 6/2007 | Ruiz et al. |
| 7,234,465 B2 | 6/2007 | Wood |
| 7,237,205 B2 | 6/2007 | Sarel |
| 7,246,620 B2 | 7/2007 | Conroy, Jr. |
| D549,323 S | 8/2007 | Kwok et al. |
| 7,255,103 B2 | 8/2007 | Bassin |
| 7,255,107 B1 | 8/2007 | Gomez |
| 7,267,122 B2 | 9/2007 | Hill |
| 7,267,123 B2 | 9/2007 | Aylsworth et al. |
| 7,270,126 B2 | 9/2007 | Wallace et al. |
| 7,270,128 B2 | 9/2007 | Berthon-Jones et al. |
| 7,296,569 B2 | 11/2007 | Frye et al. |
| 7,296,573 B2 | 11/2007 | Estes et al. |
| D557,802 S | 12/2007 | Miceli, Jr. et al. |
| 7,302,950 B2 | 12/2007 | Berthon-Jones et al. |
| 7,305,987 B2 | 12/2007 | Scholler et al. |
| 7,318,437 B2 | 1/2008 | Gunaratnam et al. |
| 7,320,321 B2 | 1/2008 | Pranger et al. |
| 7,328,703 B1 | 2/2008 | Tiep |
| 7,353,826 B2 | 4/2008 | Sleeper et al. |
| 7,367,337 B2 | 5/2008 | Berthon-Jones et al. |
| 7,370,652 B2 | 5/2008 | Matula, Jr. et al. |
| 7,373,939 B1 | 5/2008 | DuBois et al. |
| 7,406,966 B2 | 8/2008 | Wondka |
| 7,418,965 B2 | 9/2008 | Fukunaga et al. |
| 7,422,015 B2 | 9/2008 | Delisle et al. |
| 7,431,035 B2 | 10/2008 | Mizuta et al. |
| 7,451,762 B2 | 11/2008 | Chua et al. |
| 7,455,717 B2 | 11/2008 | Sprinkle |
| 7,461,656 B2 | 12/2008 | Gunaratnam et al. |
| 7,468,040 B2 | 12/2008 | Hartley et al. |
| 7,469,697 B2 | 12/2008 | Lee et al. |
| 7,472,702 B2 | 1/2009 | Beck et al. |
| 7,478,641 B2 | 1/2009 | Rousselet |
| 7,481,219 B2 | 1/2009 | Lewis et al. |
| 7,481,221 B2 | 1/2009 | Kullik et al. |
| 7,487,774 B2 | 2/2009 | Acker |
| 7,487,778 B2 | 2/2009 | Freitag |
| 7,490,605 B2 | 2/2009 | Frye et al. |
| D588,258 S | 3/2009 | Judson et al. |
| D589,139 S | 3/2009 | Guney et al. |
| 7,500,482 B2 | 3/2009 | Biederman |
| 7,509,957 B2 | 3/2009 | Duquette et al. |
| D591,419 S | 4/2009 | Chandran et al. |
| 7,533,670 B1 | 5/2009 | Freitag et al. |
| 7,556,038 B2 | 7/2009 | Kirby et al. |
| 7,559,327 B2 | 7/2009 | Hernandez |
| 7,562,657 B2 | 7/2009 | Blanch et al. |
| 7,562,659 B2 | 7/2009 | Matarasso |
| 7,578,294 B2 | 8/2009 | Pierro et al. |
| 7,588,033 B2 | 9/2009 | Wondka |
| 7,591,265 B2 | 9/2009 | Lee et al. |
| 7,631,642 B2 | 12/2009 | Freitag et al. |
| 7,640,934 B2 | 1/2010 | Zollinger et al. |
| 7,658,189 B2 | 2/2010 | Davidson et al. |
| D614,288 S | 4/2010 | Judson et al. |
| 7,721,733 B2 | 5/2010 | Hughes et al. |
| 7,721,736 B2 | 5/2010 | Urias et al. |
| 7,740,013 B2 | 6/2010 | Ishizaki et al. |
| 7,743,770 B2 | 6/2010 | Curti et al. |
| 7,762,253 B2 | 7/2010 | Acker et al. |
| 7,766,009 B2 | 8/2010 | Frye et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,841,343 B2 | 11/2010 | Deane et al. |

| Patent No. | Date | Inventor |
|---|---|---|
| 7,845,350 B1 | 12/2010 | Kayyali et al. |
| 7,849,854 B2 | 12/2010 | DeVries et al. |
| 7,856,982 B2 | 12/2010 | Matula, Jr. et al. |
| 7,866,318 B2 | 1/2011 | Bassin |
| 7,874,290 B2 | 1/2011 | Chalvignac |
| 7,874,291 B2 | 1/2011 | Ging et al. |
| 7,874,293 B2 | 1/2011 | Gunaratnam et al. |
| 7,878,980 B2 | 2/2011 | Ricciardelli |
| 7,882,834 B2 | 2/2011 | Gradon et al. |
| 7,886,740 B2 | 2/2011 | Thomas et al. |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,900,628 B2 | 3/2011 | Matula, Jr. et al. |
| 7,900,635 B2 | 3/2011 | Gunaratnam et al. |
| 7,901,361 B2 | 3/2011 | Rapoport et al. |
| 7,905,231 B2 | 3/2011 | Chalvignac |
| 7,913,691 B2 | 3/2011 | Farrugia |
| 7,914,459 B2 | 3/2011 | Green et al. |
| 7,918,226 B2 | 4/2011 | Acker et al. |
| 7,926,486 B2 | 4/2011 | Childers |
| 7,926,487 B2 | 4/2011 | Drew et al. |
| 7,931,023 B2 | 4/2011 | Berthon-Jones et al. |
| 7,934,499 B2 | 5/2011 | Berthon-Jones |
| 7,938,114 B2 | 5/2011 | Matthews et al. |
| 7,942,150 B2 | 5/2011 | Guney et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham et al. |
| 7,987,850 B2 | 8/2011 | Zollinger et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 7,997,271 B2 | 8/2011 | Hickle et al. |
| 7,997,272 B2 | 8/2011 | Isaza |
| 8,001,967 B2 | 8/2011 | Wallace et al. |
| D645,557 S | 9/2011 | Scheiner et al. |
| 8,011,365 B2 | 9/2011 | Douglas et al. |
| 8,011,366 B2 | 9/2011 | Knepper |
| 8,015,971 B2 | 9/2011 | Kwok |
| 8,015,974 B2 | 9/2011 | Christopher et al. |
| 8,020,558 B2 | 9/2011 | Christopher et al. |
| 8,025,052 B2 | 9/2011 | Matthews et al. |
| RE42,843 E | 10/2011 | Strickland et al. |
| 8,042,535 B2 | 10/2011 | Kenyon et al. |
| 8,042,537 B2 | 10/2011 | Mechlenburg et al. |
| 8,042,539 B2 | 10/2011 | Chandran et al. |
| 8,042,546 B2 | 10/2011 | Gunaratnam et al. |
| 8,061,354 B2 | 11/2011 | Schneider et al. |
| 8,066,004 B2 | 11/2011 | Morris et al. |
| 2001/0035185 A1 | 11/2001 | Christopher |
| 2001/0035186 A1 | 11/2001 | Hill |
| 2001/0042548 A1 | 11/2001 | Boussignac |
| 2002/0014241 A1 | 2/2002 | Gradon et al. |
| 2002/0017300 A1 | 2/2002 | Hickle et al. |
| 2002/0020930 A1 | 2/2002 | Austin et al. |
| 2002/0026941 A1 | 3/2002 | Biondi et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0066452 A1 | 6/2002 | Kessler et al. |
| 2002/0078957 A1 | 6/2002 | Remmers et al. |
| 2002/0092527 A1 | 7/2002 | Wood |
| 2002/0112730 A1 | 8/2002 | Dutkiewicz |
| 2002/0153010 A1 | 10/2002 | Rozenberg et al. |
| 2002/0157673 A1 | 10/2002 | Kessler et al. |
| 2002/0159323 A1 | 10/2002 | Makabe et al. |
| 2002/0179090 A1 | 12/2002 | Boussignac |
| 2003/0000522 A1 | 1/2003 | Lynn et al. |
| 2003/0047185 A1 | 3/2003 | Olsen et al. |
| 2003/0069489 A1 | 4/2003 | Abreu |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0116163 A1 | 6/2003 | Wood |
| 2003/0121519 A1 | 7/2003 | Estes et al. |
| 2003/0145852 A1 | 8/2003 | Schmidt et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0213488 A1 | 11/2003 | Remmers et al. |
| 2003/0221687 A1 | 12/2003 | Kaigler |
| 2003/0230308 A1 | 12/2003 | Linden |
| 2004/0020493 A1 | 2/2004 | Wood |
| 2004/0025881 A1 | 2/2004 | Gunaratnam et al. |
| 2004/0035431 A1 | 2/2004 | Wright |
| 2004/0040560 A1 | 3/2004 | Euliano et al. |
| 2004/0050387 A1 | 3/2004 | Younes |
| 2004/0074494 A1 | 4/2004 | Frater |
| 2004/0159323 A1 | 8/2004 | Schmidt et al. |
| 2004/0206352 A1 | 10/2004 | Conroy |
| 2004/0221848 A1 | 11/2004 | Hill |
| 2004/0221854 A1 | 11/2004 | Hete et al. |
| 2004/0226566 A1 | 11/2004 | Gunaratnam et al. |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0005938 A1 | 1/2005 | Berthon-Jones et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0033247 A1 | 2/2005 | Thompson |
| 2005/0034724 A1 | 2/2005 | O'Dea |
| 2005/0061322 A1 | 3/2005 | Freitag |
| 2005/0061326 A1 | 3/2005 | Payne |
| 2005/0072430 A1 | 4/2005 | Djupesland |
| 2005/0081849 A1 | 4/2005 | Warren |
| 2005/0087190 A1 | 4/2005 | Jafari et al. |
| 2005/0098179 A1 | 5/2005 | Burton et al. |
| 2005/0103343 A1 | 5/2005 | Gosweiler |
| 2005/0121033 A1 | 6/2005 | Starr et al. |
| 2005/0121037 A1 | 6/2005 | Wood |
| 2005/0121038 A1 | 6/2005 | Christopher |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0247308 A1 | 11/2005 | Frye et al. |
| 2005/0257793 A1 | 11/2005 | Tatsumoto |
| 2005/0274381 A1 | 12/2005 | Deane et al. |
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0048781 A1 | 3/2006 | Nawata |
| 2006/0054169 A1 | 3/2006 | Han et al. |
| 2006/0070625 A1 | 4/2006 | Ayappa et al. |
| 2006/0079799 A1 | 4/2006 | Green et al. |
| 2006/0096596 A1 | 5/2006 | Occhialini et al. |
| 2006/0107958 A1 | 5/2006 | Sleeper |
| 2006/0112959 A1 | 6/2006 | Mechlenburg et al. |
| 2006/0124131 A1 | 6/2006 | Chandran et al. |
| 2006/0124134 A1 | 6/2006 | Wood |
| 2006/0137690 A1 | 6/2006 | Gunaratnam et al. |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0174877 A1 | 8/2006 | Jagger et al. |
| 2006/0180149 A1 | 8/2006 | Matarasso |
| 2006/0185669 A1 | 8/2006 | Bassovitch |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Iobbi |

| | | | | | | |
|---|---|---|---|---|---|---|
| 2006/0237013 A1 | 10/2006 | Kwok | | 2008/0283060 A1 | 11/2008 | Bassin |
| 2006/0243278 A1 | 11/2006 | Hamilton et al. | | 2008/0295846 A1 | 12/2008 | Han et al. |
| 2006/0249155 A1 | 11/2006 | Gambone | | 2008/0302364 A1 | 12/2008 | Garde et al. |
| 2006/0266361 A1 | 11/2006 | Hernandez | | 2008/0308104 A1 | 12/2008 | Blomberg et al. |
| 2007/0000490 A1 | 1/2007 | DeVries et al. | | 2009/0007911 A1 | 1/2009 | Cleary et al. |
| 2007/0000495 A1 | 1/2007 | Matula et al. | | 2009/0020121 A1 | 1/2009 | Bassin |
| 2007/0017515 A1 | 1/2007 | Wallace et al. | | 2009/0044808 A1 | 2/2009 | Guney et al. |
| 2007/0056590 A1 | 3/2007 | Wolfson | | 2009/0056708 A1 | 3/2009 | Stenzler et al. |
| 2007/0062529 A1 | 3/2007 | Choncholas et al. | | 2009/0078255 A1 | 3/2009 | Bowman et al. |
| 2007/0068528 A1 | 3/2007 | Bohm et al. | | 2009/0078258 A1 | 3/2009 | Bowman et al. |
| 2007/0074724 A1 | 4/2007 | Duquette et al. | | 2009/0095298 A1 | 4/2009 | Gunaratnam et al. |
| 2007/0089743 A1 | 4/2007 | Hoffman | | 2009/0095300 A1 | 4/2009 | McMorrow |
| 2007/0089745 A1 | 4/2007 | Gabriel et al. | | 2009/0095303 A1 | 4/2009 | Sher et al. |
| 2007/0095347 A1 | 5/2007 | Lampotang et al. | | 2009/0099471 A1 | 4/2009 | Broadley et al. |
| 2007/0107728 A1 | 5/2007 | Ricciardelli et al. | | 2009/0101147 A1 | 4/2009 | Landis et al. |
| 2007/0107732 A1 | 5/2007 | Dennis et al. | | 2009/0101154 A1 | 4/2009 | Mutti et al. |
| 2007/0107737 A1 | 5/2007 | Landis et al. | | 2009/0107502 A1 | 4/2009 | Younes |
| 2007/0113850 A1 | 5/2007 | Acker et al. | | 2009/0118632 A1 | 5/2009 | Goepp |
| 2007/0113856 A1 | 5/2007 | Acker et al. | | 2009/0120437 A1 | 5/2009 | Oates et al. |
| 2007/0125379 A1 | 6/2007 | Pierro et al. | | 2009/0126739 A1 | 5/2009 | Ng et al. |
| 2007/0137653 A1 | 6/2007 | Wood | | 2009/0133699 A1 | 5/2009 | Nalagatla et al. |
| 2007/0163600 A1 | 7/2007 | Hoffman | | 2009/0139527 A1 | 6/2009 | Ng et al. |
| 2007/0173705 A1 | 7/2007 | Teller et al. | | 2009/0145435 A1 | 6/2009 | White et al. |
| 2007/0181125 A1 | 8/2007 | Mulier | | 2009/0151719 A1 | 6/2009 | Wondka et al. |
| 2007/0193705 A1 | 8/2007 | Hsu | | 2009/0151724 A1 | 6/2009 | Wondka et al. |
| 2007/0199568 A1 | 8/2007 | Diekens et al. | | 2009/0151726 A1 | 6/2009 | Freitag |
| 2007/0209662 A1 | 9/2007 | Bowen et al. | | 2009/0151729 A1 | 6/2009 | Judson et al. |
| 2007/0215156 A1 | 9/2007 | Kwok | | 2009/0156953 A1 | 6/2009 | Wondka et al. |
| 2007/0232950 A1 | 10/2007 | West | | 2009/0165799 A1 | 7/2009 | Duquette et al. |
| 2007/0240716 A1 | 10/2007 | Marx | | 2009/0173347 A1 | 7/2009 | Berthon-Jones |
| 2007/0251528 A1 | 11/2007 | Seitz et al. | | 2009/0173349 A1 | 7/2009 | Hernandez et al. |
| 2007/0272249 A1 | 11/2007 | Chandran et al. | | 2009/0183739 A1 | 7/2009 | Wondka |
| 2008/0000475 A1 | 1/2008 | Hill | | 2009/0199855 A1 | 8/2009 | Davenport |
| 2008/0006271 A1 | 1/2008 | Aylsworth et al. | | 2009/0205662 A1 | 8/2009 | Kwok et al. |
| 2008/0011298 A1 | 1/2008 | Mazar et al. | | 2009/0241947 A1 | 10/2009 | Bedini et al. |
| 2008/0011301 A1 | 1/2008 | Qian | | 2009/0241951 A1 | 10/2009 | Jafari et al. |
| 2008/0041371 A1 | 2/2008 | Freitag | | 2009/0250066 A1 | 10/2009 | Daly |
| 2008/0041386 A1 | 2/2008 | Dodier et al. | | 2009/0255533 A1 | 10/2009 | Freitag et al. |
| 2008/0045815 A1 | 2/2008 | Derchak et al. | | 2009/0260625 A1 | 10/2009 | Wondka |
| 2008/0047559 A1 | 2/2008 | Fiori | | 2009/0277452 A1 | 11/2009 | Lubke et al. |
| 2008/0051674 A1 | 2/2008 | Davenport et al. | | 2009/0293877 A1 | 12/2009 | Blanch et al. |
| 2008/0053438 A1 | 3/2008 | DeVries et al. | | 2009/0301495 A1 | 12/2009 | Pierro et al. |
| 2008/0053447 A1 | 3/2008 | Ratajczak et al. | | 2009/0308395 A1 | 12/2009 | Lee et al. |
| 2008/0060646 A1 | 3/2008 | Isaza | | 2009/0320851 A1 | 12/2009 | Selvarajan et al. |
| 2008/0060657 A1 | 3/2008 | McAuley et al. | | 2010/0043786 A1 | 2/2010 | Freitag et al. |
| 2008/0066753 A1 | 3/2008 | Martin et al. | | 2010/0071693 A1 | 3/2010 | Allum et al. |
| 2008/0072902 A1 | 3/2008 | Setzer et al. | | 2010/0071697 A1 | 3/2010 | Jafari et al. |
| 2008/0078392 A1 | 4/2008 | Pelletier et al. | | 2010/0083968 A1 | 4/2010 | Wondka et al. |
| 2008/0078407 A1 | 4/2008 | Sherman | | 2010/0108073 A1 | 5/2010 | Zollinger et al. |
| 2008/0092904 A1 | 4/2008 | Gunaratnam et al. | | 2010/0132716 A1 | 6/2010 | Selvarajan et al. |
| 2008/0092905 A1 | 4/2008 | Gunaratnam et al. | | 2010/0132717 A1 | 6/2010 | Davidson et al. |
| 2008/0092906 A1 | 4/2008 | Gunaratnam et al. | | 2010/0163043 A1 | 7/2010 | Hart et al. |
| 2008/0099024 A1 | 5/2008 | Gunaratnam et al. | | 2010/0170512 A1 | 7/2010 | Kuypers et al. |
| 2008/0099027 A1 | 5/2008 | Gunaratnam et al. | | 2010/0170513 A1 | 7/2010 | Bowditch et al. |
| 2008/0105264 A1 | 5/2008 | Gunaratnam et al. | | 2010/0192957 A1 | 8/2010 | Hobson et al. |
| 2008/0110462 A1 | 5/2008 | Chekal et al. | | 2010/0218766 A1 | 9/2010 | Milne |
| 2008/0121230 A1 | 5/2008 | Cortez et al. | | 2010/0224196 A1 | 9/2010 | Jablons |
| 2008/0135044 A1 | 6/2008 | Freitag et al. | | 2010/0252037 A1 | 10/2010 | Wondka et al. |
| 2008/0142019 A1 | 6/2008 | Lewis et al. | | 2010/0252039 A1 | 10/2010 | Cipollone et al. |
| 2008/0161653 A1 | 7/2008 | Lin et al. | | 2010/0252040 A1 | 10/2010 | Kapust et al. |
| 2008/0173304 A1 | 7/2008 | Zaiser et al. | | 2010/0252041 A1 | 10/2010 | Kapust et al. |
| 2008/0178880 A1 | 7/2008 | Christopher et al. | | 2010/0252042 A1 | 10/2010 | Kapust et al. |
| 2008/0178881 A1 | 7/2008 | Whitcher et al. | | 2010/0252043 A1 | 10/2010 | Freitag |
| 2008/0178882 A1 | 7/2008 | Christopher et al. | | 2010/0252044 A1 | 10/2010 | Duquette et al. |
| 2008/0185002 A1 | 8/2008 | Berthon-Jones et al. | | 2010/0275920 A1 | 11/2010 | Tham et al. |
| 2008/0185007 A1 | 8/2008 | Sleeper et al. | | 2010/0275921 A1 | 11/2010 | Schindhelm et al. |
| 2008/0190429 A1 | 8/2008 | Tatarek | | 2010/0282251 A1 | 11/2010 | Calluaud et al. |
| 2008/0190436 A1 | 8/2008 | Jaffe et al. | | 2010/0282810 A1 | 11/2010 | Hawes |
| 2008/0196715 A1 | 8/2008 | Yamamori | | 2010/0288279 A1 | 11/2010 | Seiver et al. |
| 2008/0196723 A1 | 8/2008 | Tilley | | 2010/0288289 A1 | 11/2010 | Nasir |
| 2008/0196728 A1 | 8/2008 | Ho | | 2010/0300445 A1 | 12/2010 | Chatburn et al. |
| 2008/0202528 A1 | 8/2008 | Carter et al. | | 2010/0300446 A1 | 12/2010 | Nicolazzi et al. |
| 2008/0216834 A1 | 9/2008 | Easley et al. | | 2010/0307487 A1 | 12/2010 | Dunsmore et al. |
| 2008/0216838 A1 | 9/2008 | Wondka | | 2010/0307495 A1 | 12/2010 | Kepler et al. |
| 2008/0216841 A1 | 9/2008 | Grimes et al. | | 2010/0307499 A1 | 12/2010 | Eger et al. |
| 2008/0223369 A1 | 9/2008 | Warren | | 2010/0307500 A1 | 12/2010 | Armitstead |
| 2008/0245369 A1 | 10/2008 | Matula et al. | | 2010/0307502 A1 | 12/2010 | Rummery et al. |
| 2008/0251079 A1 | 10/2008 | Richey | | 2010/0313891 A1 | 12/2010 | Veliss et al. |
| 2008/0264417 A1 | 10/2008 | Manigel et al. | | 2010/0313898 A1 | 12/2010 | Richard et al. |

| | | | |
|---|---|---|---|
| 2010/0319703 A1 | 12/2010 | Hayman et al. | |
| 2010/0326441 A1 | 12/2010 | Zucker et al. | |
| 2010/0326446 A1 | 12/2010 | Behlmaier | |
| 2011/0000489 A1 | 1/2011 | Laksov et al. | |
| 2011/0009763 A1 | 1/2011 | Levitsky et al. | |
| 2011/0011402 A1 | 1/2011 | Berthon-Jones | |
| 2011/0023878 A1 | 2/2011 | Thiessen | |
| 2011/0023881 A1 | 2/2011 | Thiessen | |
| 2011/0034819 A1 | 2/2011 | Desforges et al. | |
| 2011/0036352 A1 | 2/2011 | Estes et al. | |
| 2011/0041850 A1 | 2/2011 | Vandine et al. | |
| 2011/0041855 A1 | 2/2011 | Gunaratnam et al. | |
| 2011/0061647 A1 | 3/2011 | Stahmann et al. | |
| 2011/0067704 A1 | 3/2011 | Kooij et al. | |
| 2011/0067709 A1 | 3/2011 | Doshi et al. | |
| 2011/0071444 A1 | 3/2011 | Kassatly et al. | |
| 2011/0073107 A1 | 3/2011 | Rodman et al. | |
| 2011/0073116 A1 | 3/2011 | Genger et al. | |
| 2011/0087123 A9 | 4/2011 | Choncholas et al. | |
| 2011/0088690 A1 | 4/2011 | Djupesland et al. | |
| 2011/0094518 A1 | 4/2011 | Cipollone et al. | |
| 2011/0100365 A1 | 5/2011 | Wedler et al. | |
| 2011/0114098 A1 | 5/2011 | McAuley et al. | |
| 2011/0125052 A1 | 5/2011 | Davenport et al. | |
| 2011/0126841 A1 | 6/2011 | Matula, Jr. et al. | |
| 2011/0132363 A1 | 6/2011 | Chalvignac | |
| 2011/0139153 A1 | 6/2011 | Chalvignac | |
| 2011/0146687 A1 | 6/2011 | Fukushima | |
| 2011/0155140 A1 | 6/2011 | Ho et al. | |
| 2011/0162650 A1 | 7/2011 | Miller et al. | |
| 2011/0162655 A1 | 7/2011 | Gunaratnam et al. | |
| 2011/0178419 A1 | 7/2011 | Wood et al. | |
| 2011/0180068 A1 | 7/2011 | Kenyon et al. | |
| 2011/0197885 A1 | 8/2011 | Wondka et al. | |
| 2011/0209705 A1 | 9/2011 | Freitag | |
| 2011/0214676 A1 | 9/2011 | Allum et al. | |
| 2011/0220105 A1 | 9/2011 | Meier | |
| 2011/0232642 A1 | 9/2011 | Bliss et al. | |
| 2011/0247625 A1 | 10/2011 | Boussignac | |
| 2011/0253147 A1 | 10/2011 | Gusky et al. | |
| 2011/0259327 A1 | 10/2011 | Wondka et al. | |
| 2011/0265796 A1 | 11/2011 | Amarasinghe et al. | |
| 2011/0277765 A1 | 11/2011 | Christopher et al. | |
| 2011/0284003 A1 | 11/2011 | Douglas et al. | |

FOREIGN PATENT DOCUMENTS

| | | |
|---|---|---|
| DE | 19841070 | 5/2000 |
| DE | 19849571 | 5/2000 |
| DE | 10337138.9 | 3/2005 |
| DE | 10 2006 023 637.8 | 11/2007 |
| EP | 0125424 | 11/1984 |
| EP | 0692273 | 1/1996 |
| EP | 0778035 | 6/1997 |
| EP | 1359961 | 11/2003 |
| EP | 2377462 | 11/2010 |
| GB | 2174609 | 11/1986 |
| GB | 2201098 | 8/1988 |
| GB | 1055148 | 6/1989 |
| GB | 2338420 | 12/1999 |
| JP | S63-57060 | 3/1998 |
| JP | 2002-204830 | 7/2002 |
| WO | WO-92/11054 | 7/1992 |
| WO | WO-98/01176 | 1/1998 |
| WO | WO-99/04841 | 2/1999 |
| WO | WO-00/64521 | 11/2000 |
| WO | WO-01/76655 | 10/2001 |
| WO | WO-02/062413 | 8/2002 |
| WO | WO-2004/009169 | 1/2004 |
| WO | WO-2005/014091 | 2/2005 |
| WO | WO-2005/018524 | 3/2005 |
| WO | WO-2006/138580 | 12/2006 |
| WO | WO-2007/035804 | 3/2007 |
| WO | WO-2007/139531 | 12/2007 |
| WO | WO-2007142812 | 12/2007 |
| WO | WO-2008/014543 | 2/2008 |
| WO | WO-2008/019102 | 2/2008 |
| WO | WO-2008/052534 | 5/2008 |
| WO | WO-2008/112474 | 9/2008 |
| WO | WO-2008/138040 | 11/2008 |
| WO | WO-2008/144589 | 11/2008 |
| WO | WO-2008/144669 | 11/2008 |
| WO | WO-2009/042973 | 4/2009 |
| WO | WO-2009/042974 | 4/2009 |
| WO | WO-2009/059353 | 5/2009 |
| WO | WO-2009/064202 | 5/2009 |
| WO | WO-2009/074160 | 6/2009 |
| WO | WO-2009/082295 | 7/2009 |
| WO | WO-2009/087607 | 7/2009 |
| WO | WO-2009/092057 | 7/2009 |
| WO | WO-2009/103288 | 8/2009 |
| WO | WO-2009/109005 | 9/2009 |
| WO | WO-2009/115944 | 9/2009 |
| WO | WO-2009/115948 | 9/2009 |
| WO | WO-2009/115949 | 9/2009 |
| WO | WO-2009/129506 | 10/2009 |
| WO | WO-2009/136101 | 11/2009 |
| WO | WO-2009/139647 | 11/2009 |
| WO | WO-2009/149351 | 12/2009 |
| WO | WO-2009/149353 | 12/2009 |
| WO | WO-2009/149355 | 12/2009 |
| WO | WO-2009/149357 | 12/2009 |
| WO | WO-2009/151344 | 12/2009 |
| WO | WO-2009/151791 | 12/2009 |
| WO | WO-2010/000135 | 1/2010 |
| WO | WO-2010/021556 | 2/2010 |
| WO | WO-2010/022363 | 2/2010 |
| WO | WO-2010/039989 | 4/2010 |
| WO | WO-2010/041966 | 4/2010 |
| WO | WO-2010/044034 | 4/2010 |
| WO | WO-2010/057268 | 5/2010 |
| WO | WO-2010/059049 | 5/2010 |
| WO | WO-2010/060422 | 6/2010 |
| WO | WO-2010/068356 | 6/2010 |
| WO | WO-2010/070493 | 6/2010 |
| WO | WO-2010/070497 | 6/2010 |
| WO | WO-2010/070498 | 6/2010 |
| WO | WO-2010/076711 | 7/2010 |
| WO | WO-2010/081223 | 7/2010 |
| WO | WO-2010/091157 | 8/2010 |
| WO | WO-2010/099375 | 9/2010 |
| WO | WO-2010/102094 | 9/2010 |
| WO | WO-2010/115166 | 10/2010 |
| WO | WO-2010/115168 | 10/2010 |
| WO | WO-2010/115169 | 10/2010 |
| WO | WO-2010/115170 | 10/2010 |
| WO | WO-2010/116275 | 10/2010 |
| WO | WO-2010/132853 | 11/2010 |
| WO | WO-2010/136923 | 12/2010 |
| WO | WO-2010/139014 | 12/2010 |
| WO | WO-2010/150187 | 12/2010 |
| WO | WO-2011/002608 | 1/2011 |
| WO | WO-2011/004274 | 1/2011 |
| WO | WO-2011/006184 | 1/2011 |
| WO | WO-2011/006199 | 1/2011 |
| WO | WO-2011/014931 | 2/2011 |
| WO | WO-2011/017033 | 2/2011 |
| WO | WO-2011/017738 | 2/2011 |
| WO | WO-2011/021978 | 2/2011 |
| WO | WO-2011/022779 | 3/2011 |
| WO | WO-2011/024383 | 3/2011 |
| WO | WO-2011/029073 | 3/2011 |
| WO | WO-2011/029074 | 3/2011 |
| WO | WO-2011/035373 | 3/2011 |
| WO | WO-2011/038950 | 4/2011 |
| WO | WO-2011/038951 | 4/2011 |
| WO | WO-2011/044627 | 4/2011 |
| WO | WO-2011/057362 | 5/2011 |
| WO | WO 2011/059346 | 5/2011 |
| WO | WO-2011/061648 | 5/2011 |
| WO | WO-2011/062510 | 5/2011 |
| WO | WO-2011/086437 | 7/2011 |
| WO | WO-2011/086438 | 7/2011 |
| WO | WO-2011/112807 | 9/2011 |

OTHER PUBLICATIONS

In the U.S. Patent and Trademark Office, Supplemental Notice of Allowance dated in re: U.S. Appl. No. 10/771,803, dated Nov. 7, 2008, 2 pages.

In the U.S. Patent and Trademark Office, Examiner's Interview Summary in re: U.S. Appl. No. 10/771,803, dated Oct. 31, 2008, 4 pages.
In the U.S. Patent and Trademark Office, Notice of Allowance dated in re: U.S. Appl. No. 10/771,803, dated Oct. 20, 2008, 8 pages.
In the U.S. Patent and Trademark Office, Examiner's Interview Summary in re: U.S. Appl. No. 10/771,803, dated Nov. 2, 2007, 2 pages.
In the U.S. Patent and Trademark Office, Office Action in re: U.S. Appl. No. 10/771,803, dated Jun. 14, 2007, 12 pages.
In the U.S. Patent and Trademark Office, Restriction Requirement in re: U.S. Appl. No. 12/271,484, dated Feb. 9, 2011, 5 pages.
In the U.S. Patent and Trademark Office, Non-Final Office Action dated in re: U.S. Appl. No. 10/567,746, dated Oct. 5, 2009, 9 pages.
In the U.S. Patent and Trademark Office, Notice of Allowance and Examiner's Interview Summary in re: U.S. Appl. No. 11/523,519, dated Jan. 16, 2009, 10 pages.
In the U.S. Patent and Trademark Office, Examiner's Interview Summary in re: U.S. Appl. No. 11/523,519, dated Jan. 13, 2009, 4 pages.
In the U.S. Patent and Trademark Office, Final Office Action in re: U.S. Appl. No. 11/523,519, dated Jul. 11, 2008, 13 pages.
In the U.S. Patent and Trademark Office, Examiner's Interview Summary in re: U.S. Appl. No. 11/523,519, dated Apr. 10, 2008, 3 pages.
In the U.S. Patent and Trademark Office, Final Office Action in re: U.S. Appl. No. 11/523,519, dated Nov. 26, 2007, 14 pages.
In the U.S. Patent and Trademark Office, Office Action in re: U.S. Appl. No. 11/523,519, dated Mar. 7, 2007, 11 pages.
In the U.S. Patent and Trademark Office, Restriction Requirement in re: U.S. Appl. No. 11/523,518, dated Dec. 30, 2009, 4 pages.
In the U.S. Patent and Trademark Office, Supplemental Notice of Allowance in re: U.S. Appl. No. 11/798,965, dated Aug. 21, 2009, 4 pages.
In the U.S. Patent and Trademark Office, Notice of Allowance in re: U.S. Appl. No. 11/798,965, dated Jul. 17, 2009, 5 pages.
In the U.S. Patent and Trademark Office, Final Office Action in re: U.S. Appl. No. 11/798,965, dated Apr. 9, 2009, 6 pages.
In the U.S. Patent and Trademark Office, Office Action in re: U.S. Appl. No. 11/798,965, dated Jul. 29, 2008, 12 pages.
In the U.S. Patent and Trademark Office, Office Action in re: U.S. Appl. No. 12/578,283, dated Oct. 19, 2011, 5 pages.
In the U.S. Patent and Trademark Office, Restriction/Election Requirement in re: U.S. Appl. No. 11/882,530, dated Apr. 27, 2011, 5 pages.
In the U.S. Patent and Trademark Office, Supplemental Notice of Allowance in re: U.S. Appl. No. 10/870,849, dated Jun. 16, 2009, 2 pages.
In the U.S. Patent and Trademark Office, Notice of Allowance in re: U.S. Appl. No. 10/870,849, dated Jun. 3, 2009, 4 pages.
In the U.S. Patent and Trademark Office, Notice of Allowance in re: U.S. Appl. No. 10/870,849, dated May 14, 2009, 8 pages.
In the U.S. Patent and Trademark Office, Restriction in re: U.S. Appl. No. 10/870,849, dated Nov. 16, 2007, 5 pages.
In the U.S. Patent and Trademark Office, Examiner's Interview Summary in re: U.S. Appl. No. 10/870,849, dated Jul. 27, 2007, 2 pages.
In the U.S. Patent and Trademark Office, Office Action in re: U.S. Appl. No. 10/870,849, dated Feb. 22, 2007, 13 pages.
In the U.S. Patent and Trademark Office, Restriction/Election Requirement in re: U.S. Appl. No. 12/493,677, dated Aug. 5, 2011, 5 pages.
In the U.S. Patent and Trademark Office, Restriction/Election Requirement in re: U.S. Appl. No. 12/153,423, dated Oct. 6, 2011, 8 pages.
In the U.S. Patent and Trademark Office, Notice of Allowance in re: U.S. Appl. No. 10/922,054, dated Feb. 12, 2008, 6 pages.
In the U.S. Patent and Trademark Office, Final Office Action in re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.
In the U.S. Patent and Trademark Office, Restriction Requirement in re: U.S. Appl. No. 10/922,054, dated May 17, 2006, 5 pages.
In the U.S. Patent and Trademark Office, Notice of Allowance and Examiner's Interview Summary in re: U.S. Appl. No. 12/076,062, dated Nov. 2, 2011, 8 pages.

In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, Ex Parte Quayle Office Action in re: U.S. Appl. No. 29/388,700, dated Oct. 7, 2011, 5 pages.
"AARC Clinical Practice Guideline: Oxygen Therapy in the Home or Extended Care Facility," Resp. Care, 1992: 37(8), pp. 918-922.
"ATS Statement: Guidelines for the Six-Minute Walk Test," Am. J. Respir. Crit. Care Med., 2002: 166, pp. 111-117.
"Passy-Muir Speaking Valves," Respiratory, Nov. 13, 1998, 7 pages.
Ambrosino, "Exercise and noninvasive ventilatory support," Monaldi Arch Chest Dis., 2000: 55(3): 242-246.
Ambrosino, "Weaning and Respiratory Muscle Dysfunction: The Egg Chicken Dilemma," Chest, 2005: 128(2), pp. 481-483.
Bach et al., "Intermittent Positive Pressure Ventilation via Nasal Access in the Management of Respiratory Insufficiency," Chest, 1987: 92(1), pp. 168-170.
Banner et al., "Extubating at a Pressure Support Ventilation Level Corresponding to Zero Imposed Work of Breathing," Anesthesiology, Sep. 1994: 81(3A), p. A271.
Banner et al., "Imposed Work of Breathing and Methods of Triggering a Demand-Flow, Continuous Positive Airway Pressure System," Critical Care Medicine, 1993: 21(2), pp. 183-190.
Banner et al., "Site of Pressure Measurement During Spontaneous Breathing with Continuous Positive Airway Pressure: Effect on Calculating Imposed Work of Breathing," Critical Care Medicine, 1992: 20(4), pp. 528-533.
Barakat et al., "Effect of noninvasive ventilatory support during exercise of a program in pulmonary rehabilitation in patients with COPD," Int. J. Chron. Obstruct. Pulmon. Dis., 2007: 2(4), pp. 585-591.
Barreiro et al., "Noninvasive ventilation," Crit Care Clin., 2007; 23(2): 201-22.
Bauer et al., "ADAM Nasal CPAP Circuit Adaptation: A Case Report," Sleep, 1991: 14(3), pp. 272-273.
Blanch, "Clinical Studies of Tracheal Gas Insufflation," Resp. Care, 2001: 45(2), pp. 158-166.
Borghi-Silva et al., "Non-invasive ventilation improves peripheral oxygen saturation and reduces fatigability of quadriceps in patients with COPD," Respirology, 2009, 14:537-546.
Bossi et al., "Continuous Positive Airway Pressure in the Spontaneously Breathing Newborn by Means of Bilateral Nasal Cannulation," Monatsschr Kinderheilkd, 1975: 123(4), pp. 141-146.
Boussarsar et al., "Relationship between ventilatory settings and barotrauma in the acute respiratory distress syndrome," Intensive Care Med., 2002: 28(4): 406-13.
Chang et al., "Reduced Inspiratory Muscle Endurance Following Successful Weaning From Prolonged Mechanical Ventilation," Chest, 2005: 128(2), pp. 553-559.
Charlotte Regional Medical Center, "Application of the Passy-Muir Tracheostomy and Ventilator," Speech-Language Pathology Department, Jan. 1995, 8 pages.
Christopher et al., "Preliminary Observations of Transtracheal Augmented Ventilation for Chronic Severe Respiratory Disease," Resp. Care, 2001: 46(1), pp. 15-25.
Christopher, et al., "Transtracheal Oxygen Therapy for Refractory Hypoxemia," JAMA, 1986: 256(4), pp. 494-497.
Ciccolella et al.; "Administration of High-Flow, Vapor-phased, Humidified Nasal Cannula Air (HF-HNC) Decreases Work of Breathing (WOB) in Healthy Subjects During Exercise," AmJRCCM, Apr. 2001: 163(5), Part 2, pp. A622. (Abstract Only).
Clini et al., "The Italian multicentre study on noninvasive ventilation in chronic obstructive pulmonary disease patients," Eur. Respir. J., 2002, 20(3): 529-538.
Costa et al., "Influence of noninvasive ventilation by BiPAP® on exercise tolerance and respiratory muscle strength in chronic obstructive pulmonary disease patients (COPD)," Rev. Lat. Am. Enfermagem., 2006: 14(3), pp. 378-382.
Díaz et al., "Breathing Pattern and Gas Exchange at Peak Exercise in COPD Patients With and Without Tidal Flow Limitation at Rest," European Respiratory Journal, 2001: 17, pp. 1120-1127.

Enright, "The six-minute walk test," *Resp. Care*, 2003: 8, pp. 783-785.
Ferreira et al., "Trigger Performance of Mid-level ICU Mechanical Ventilators During Assisted Ventilation: A Bench Study," *Intensive Care Medicine*, 2008,34:1669-1675.
Fink, "Helium-Oxygen: An Old Therapy Creates New Interest," *J. Resp. Care. Pract. now RT for Decision Makers in Respiratory Care*, 1999, pp. 71-76.
Gaughan et al., "A Comparison in a Lung Model of Low- and High-Flow Regulators for Transtracheal Jet Ventilation," *Anesthesiology*, 1992: 77(1), pp. 189-199.
Gregoretti, et al., "Transtracheal Open Ventilation in Acute Respiratory Failure Secondary to Severe Chronic Obstructive Pulmonary Disease Exacerbation," *Am. J. Resp. Crit. Care. Med.*, 2006: 173(8), pp. 877-881.
Haenel et al., "Efficacy of Selective Intrabronchial Air Insufflation in Acute Lobar Colapse," *Am. J. Surg.*, 1992: 164(5), pp. 501-505.
Keilty et al., "Effect of inspiratory pressure support on exercise tolerance and breathlessness in patients with severe stable chronic obstructive pulmonary disease," *Thorax*, 1994, 49(10): 990-994.
Köhnlein et al., "Noninvasive ventilation in pulmonary rehabilitation of COPD patients," *Respir. Med.*, 2009, 103: 1329-1336.
Koska et al., "Evaluation of a Fiberoptic System for Airway Pressure Monitoring," *J. Clin. Monit.*, 1993: 10(4), pp. 247-250.
Lewis, "Breathless No More, Defeating Adult Sleep Apnea," *FDA Consumer Magazine*, Jun. 1992, pp. 33-37.
Limberg et al., "Changes in Supplemental Oxygen Prescription in Pulmonary Rehabilitation," *Resp. Care*, 2006:51(11), p. 1302.
MacInryre, "Long-Term Oxygen Therapy: Conference Summary," *Resp. Care*, 2000: 45(2), pp. 237-245.
MacIntyre et al., "Acute exacerbations and repiratory failure in chronic obstructive pulmonary disease," *Proc. Am. Thorac. Soc.*, 2008: 5(4), pp. 530-535.
Massie et al., "Clinical Outcomes Related to Interface Type in Patients With Obstructive Sleep Apnea/Hypopnea Syndrome Who Are Using Continuous Positive Airway Pressure," *Chest*, 2003: 123(4), pp. 1112-1118.
McCoy, "Oxygen Conservation Techniques and Devices," *Resp. Care*, 2000: 45(1), pp. 95-104.
McGinley, "A nasal cannula can be used to treat obstructive sleep apnea"; *Am. J. Resp. Crit. Care Med.*, 2007: 176(2), pp. 194-200.
Menadue et al., "Non-invasive ventilation during arm exercise and ground walking in patients with chronic hypercapnic respiratory failure," *Respirology*, 2009, 14(2): 251-259.
Menon et al., "Tracheal Perforation. A Complication Associated with Transtracheal Oxygen Therapy," *Chest*, 1993: 104(2), pp. 636-637.
Messinger et al., "Tracheal Pressure Triggering a Demand-Flow CPAP System Decreases Work of Breathing," Anesthesiology, 1994: 81(3A), p. A272.
Messinger et al., "Using Tracheal Pressure to Trigger the Ventilator and Control Airway Pressure During Continuous Positive Airway Pressure Decreases Work of Breathing," *Chest*, 1995: vol. 108(2), pp. 509-514.
Mettey, "Use of CPAP Nasal Cannula for Aids of the Newborns in Tropical Countries," *Medecine Tropicale*, 1985: 45(1), pp. 87-90.
Nahmias et al., "Treatment of the Obstructive Sleep Apnea Syndrome Using a Nasopharyngeal Tube", *Chest*, 1988:94(6), pp. 1142-1147.
Nava et al., "Non-invasive ventilation," *Minerva Anestesiol.*, 2009: 75(1-2), pp. 31-36.
Passy-Muir Inc., "Clinical Inservice Outline", Apr. 2004, 19 pages.
Peters et al., "Combined Physiological Effects of Bronchodilators and Hyperoxia on Exertional Dyspnea in Normoxic COPD," *Thorax*, 2006: 61, pp. 559-567.
Polkey et al., "Inspiratory pressure support reduces slowing of inspiratory muscle relations rate during exhaustive treadmill walking in sever COPD," *Am. J. Resp. Crit. Care Med.*, 1996: 154(4, 10), pp. 1146-1150.
Porta et al., "Mask proportional assist vs pressure support ventilation in patients in clinically stable condition with chronic venilatory failure," *Chest*, 2002: 122(2), pp. 479-488.
Prigent et al., "Comparative Effects of Two Ventilatory Modes on Speech in Tracheostomized Patients with Neuromuscular Disease," *Am. J. Resp. Crit. Care Med.*, 2003: 167(8), pp. 114-119.
Puente-Maestu et al., "Dyspnea, Ventilatory Pattern, and Changes in Dynamic Hyperinflation Related to the Intensity of Constant Work Rate Exercise in COPD," *Chest*, 2005: 128(2), pp. 651-656.
Ram et al., "Non-invasive positive pressure ventilation for treatment of respiratory failure due to exacerbations of chroic obstructive pulmonary disease," *Cochrane Database Syst Rev.*, 2004(3):1-72.
Rothe et al., "Near Fatal Complication of Transtracheal Oxygen Therapy with the SCOOP(R) System," *Pneumologie*, 1996: 50(10), pp. 700-702. (English Abstract provided.).
Rothfleisch et al., "Facilitation of fiberoptic nasotracheal intubation in a morbidly obese patient by simultaneous use of nasal CPAP," *Chest*, 1994, 106(1): 287-288.
Sanders et al., "CPAP via Nasal Mask: A Treatment for Occlusive Sleep Apnea," *Chest*, 1983: 83(1), pp. 144-145.
Sinderby et al., "Neural control of mechanical ventilation in respiratory failure," *Nat. Med.*, 1999: 5(12), pp. 1433-1436.
Somfay et al., "Dose-Response Effect of Oxygen on Hyperinflation and Exercise Endurance in Nonhypoxaemic COPD Patients," *Eur. Resp. J.*, 2001: 18, pp. 77-84.
Sullivan et al., "Reversal of Obstructive Sleep Apnoea by Continuous Positive Airway Pressure Applied Through the Nares," *The Lancet*, 1981: 1(8225), pp. 862-865.
Sullivan, "Home treatment of obstructive sleep apnoea with continuous positive airway pressure applied through a nose-mask," *Bull Eur Physiopathol Respir.*, 1984: 20(1), pp. 49-54.
Tiep et al., "Pulsed nasal and transtracheal oxygen delivery," *Chest*, 1990: 97, pp. 364-368.
Tsuboi et al., "Ventilatory Support During Exercise in Patients With Pulmonary Tuberculosis Sequelae," *Chest*, 1997: 112(4), pp. 1000-1007.
*VHA/DOD Clinical Practice Guideline*, "Management of Chronic Obstructive Pulmonary Disease," Aug. 1999, Ver. 1.1a, Updated Nov. 1999.
Wijkstra et al., "Nocturnal non-invasive positive pressure ventilation for stable chronic obstructive pulmonary disease," *Cochrane Database Syst. Rev.*, 2002, 3: 1-22.
Yaeger et al., "Oxygen Therapy Using Pulse and Continuous Flow With a Transtracheal Catheter and a Nasal Cannula," *Chest*, 1994: 106, pp. 854-860.
Walsh, "McGraw Hill Pocket reference Machinists' and Metalworker' Pocket Reference," *New York McGraw-Hill*, 2000, pp. 3-67, submitting 3 pages.
International Preliminary Report and Written Opinion on Patentability for PCT/DE2004/001646, dated Jul. 3, 2006.
European patent Office Search Report issued Oct. 19, 2007 in co-pending EP 04762494.
International Search Report and Written Opinion for PCT/US04/26800 issued Jun. 22, 2006.
International Search Report and Written Opinion for PCT/US07/12108, dated Aug. 8, 2008.
International Search Report and Written Opinion for PCT/US07/17400, dated Apr. 28, 2008.
International Search Report and Written Opinion for PCT/US08/64015, dated Sep. 26, 2008.
International Search Report and Written Opinion for PCT/US08/64164, dated Sep. 29, 2008.
International Search Report and Written Opinion for PCT/US08/78031, dated Nov. 24, 2008.
International Search Report and Written Opinion for PCT/US08/78033, dated Dec. 3, 2008.
International Search Report and Written Opinion for PCT/US09/054673, dated Oct. 8, 2009.
International Search Report and Written Opinion for PCT/US09/41027, dated Dec. 14, 2009.
International Search Report and Written Opinion for PCT/US09/59272, dated Dec. 2, 2009.
International Search Report and Written Opinion for PCT/US2006/036600, dated Apr. 3, 2007.
International Search Report and Written Opinion for PCT/US2009/031355 issued Mar. 11, 2009.

International Search Report and Written Opinion for PCT/US2009/041034, dated Jun. 10, 2009.
International Search Report and Written Opinion for PCT/US2010/029871, dated Jul. 12, 2010.
International Search Report and Written Opinion for PCT/US2010/029873, dated Jun. 28, 2010.
International Search Report and Written Opinion for PCT/US2010/029874, dated Jul. 12, 2010.
International Search Report and Written Opinion for PCT/US2010/029875, dated Jul. 12, 2010.
International Search Report and Written Opinion for PCT/US2010/047920, dated Nov. 1, 2010.
International Search Report and Written Opinion for PCT/US2010/047921, dated Jan. 27, 2011.
International Search Report for PCT/DE2004/001646, dated Jan. 17, 2005.

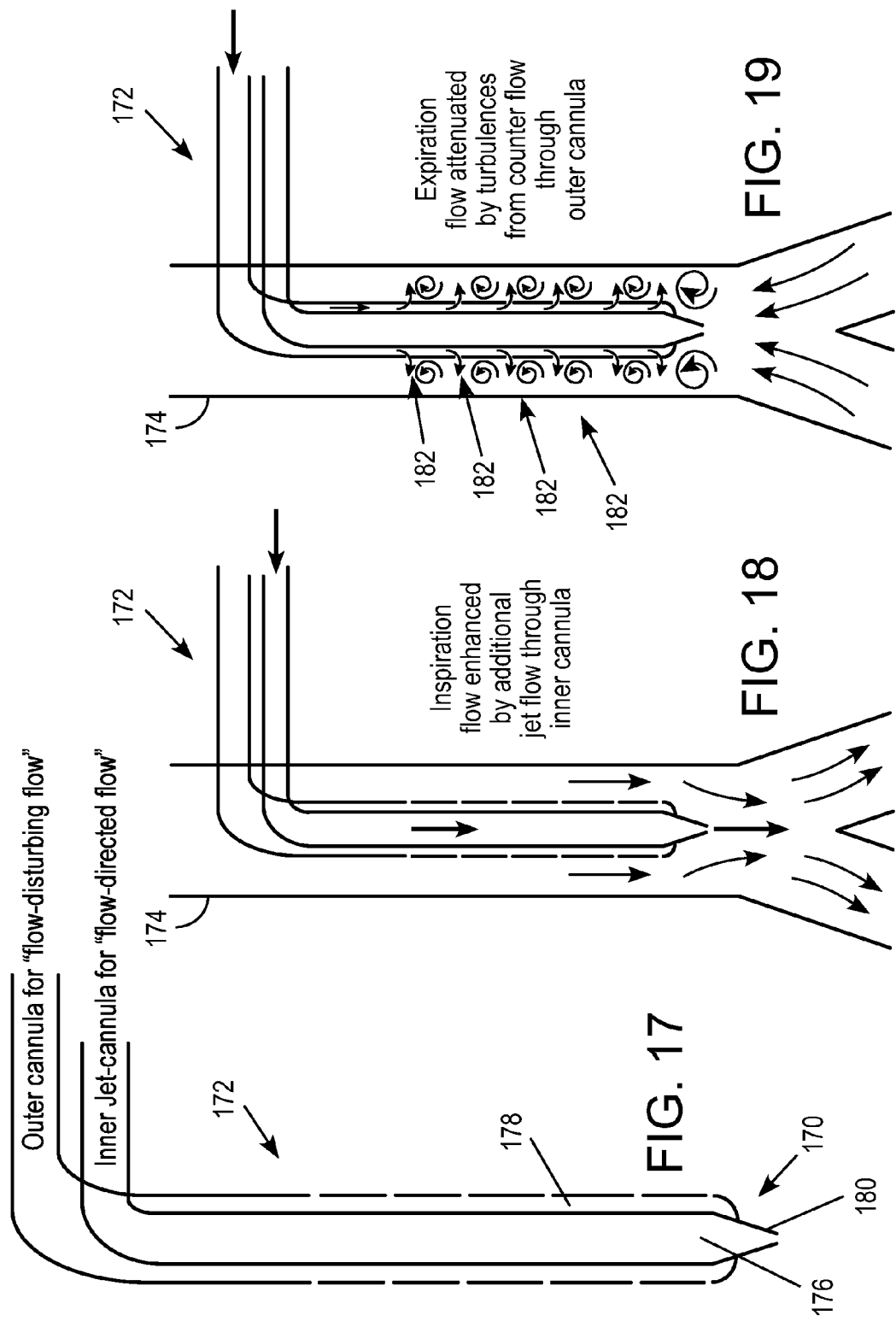

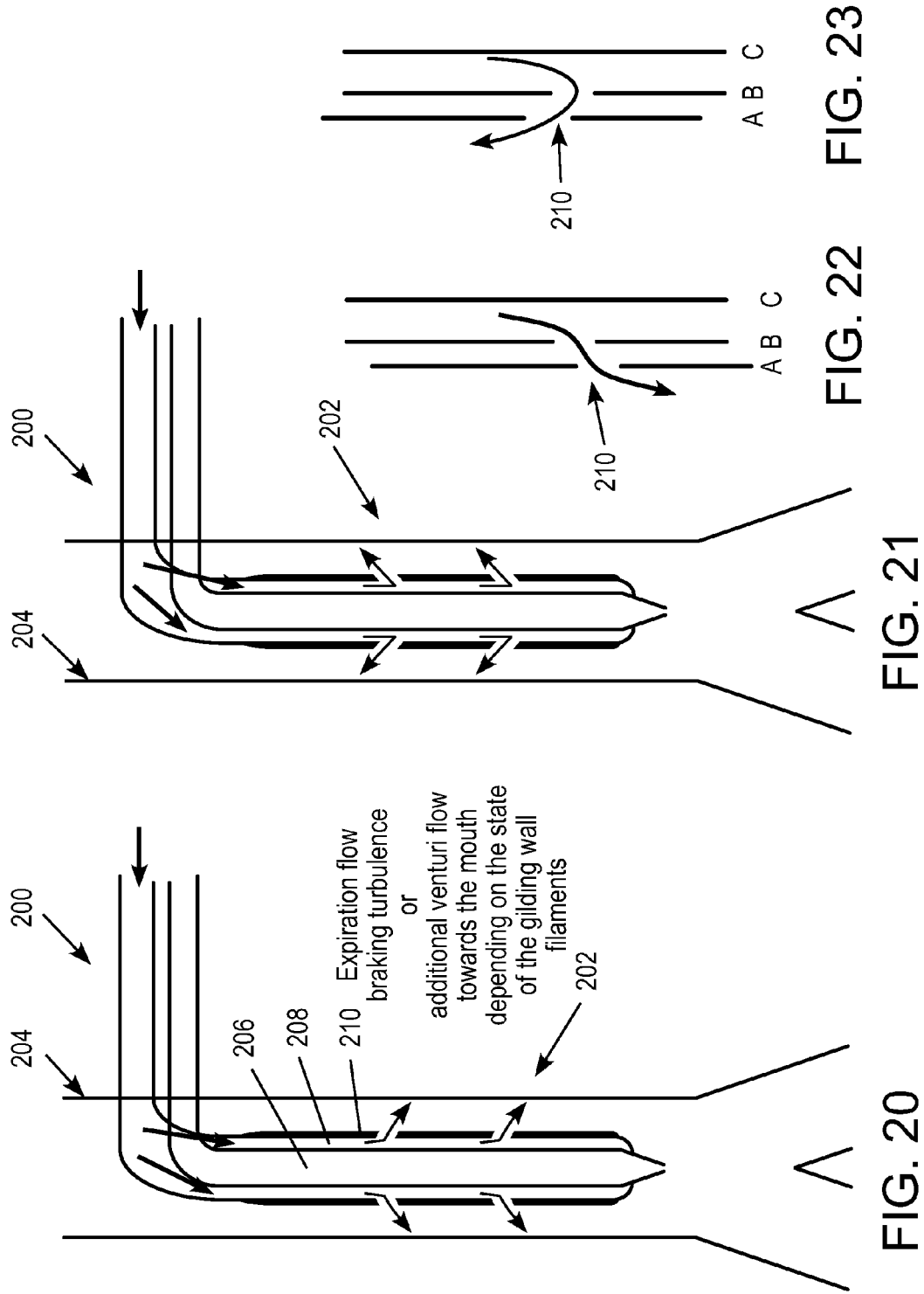

SYSTEMS, METHODS AND APPARATUS FOR RESPIRATORY SUPPORT OF A PATIENT

PRIORITY CLAIM

This patent application is a continuation of U.S. Ser. No. 11/523,518, filed Sep. 20, 2006, which is a continuation-in-part application of and claims priority to U.S. Ser. No. 10/771,803, "Tracheal Catheter and Prosthesis and Method of Respiratory Support of a Patient", filed Feb. 4, 2004, which claims priority to German Application No. 20/40963-001 (Publication 103 37 138.9), filed Aug. 11, 2003, and U.S. Ser. No. 10/567,746, "Method and Arrangement for Respiratory Support for a Patient Airway Prosthesis and Catheter", filed Feb. 10, 2006, which is a National Phase of PCT/DE2004/001646, "Method and Arrangement for Respiratory Support for a Patient Airway Prosthesis and Catheter", filed Jul. 23, 2004, which claims priority to German Application No. 20/40963-001 (Publication 103 37 138.9), "Method and Arrangement for Respiratory Support for a Patient Airway Prosthesis and Catheter", filed Aug. 11, 2003; and claims priority to U.S. Ser. No. 60/718,318, "Systems, Methods and Apparatus for Respiratory Support for a Patient", filed Sep. 20, 2005, the disclosures of all of which are incorporated herein by reference in their entireties.

FIELD OF INVENTION

The present invention relates generally to respiratory systems and more particularly to specialized systems, methods, and devices for enhanced ventilation of a patient.

BACKGROUND OF THE INVENTION

In order for the body to take in oxygen and give off carbon dioxide, two components of the respiratory bronchial system must function—the lungs as a gas-exchanging organ and the respiratory pump as a ventilation organ that transports air into the lungs and back out again. The breathing center in the brain, central and peripheral nerves, the osseous thorax and the breathing musculature as well as free, stable respiratory paths are necessary for a correct functioning of the respiratory pump.

In certain diseases there is a constant overload on or exhaustion of the respiratory pump. A typical syndrome is pulmonary emphysema with flat-standing diaphragms. Flat-standing diaphragms do not have the ability to contract. In the case of pulmonary emphysema, respiratory paths are usually extremely slack and tend to collapse. As a consequence of the flattened, over-extended diaphragms, the patient cannot inhale deeply enough. In addition, the patient cannot exhale sufficiently due to collapsing respiratory paths. This results in an insufficient respiration with an undersupply of oxygen and a rise of carbon dioxide in the blood, i.e. a ventilatory insufficiency.

The treatment for inhalation difficulty often involves a breathing device. A home ventilator is an artificial respirator for supporting or completely relieving the respiratory pump. Artificial respiration can be applied non-invasively via a nose or mouth mask that the patient can put on and take off as needed. However, the nose or mouth mask prevents the patient from breathing and speaking freely, and is very invasive.

Another treatment option is invasive ventilation. Invasive ventilation is usually applied via a cuffed endotracheal tube that is passed through the mouth and the larynx and into the windpipe, or is applied via a tracheostomy. The tracheostomy involves an opening placed in the trachea by an operation. A catheter about the diameter of a finger with a blocking balloon or cuff is inserted via the opening into the trachea and connected to a ventilator that applies cyclic positive pressure. This procedure makes sufficiently deep respiration possible, but prevents the patient from speaking.

In addition to home ventilation with a mask and invasive ventilation, there is also transtracheal administration of oxygen via thinner catheters. U.S. Pat. No. 5,181,509 or 5,279,288 disclose corresponding embodiments. In this manner, a highly dosed administration of oxygen is administered to the patient in a continuous stream with a permanently adjusted frequency. The flow rate of oxygen is regulated manually by a regulator. However, simulation of the natural breathing process of a patient is not achieved because the depth of breathing is not enhanced. Some common problems associated with these transtracheal catheters are irritations and traumas of the sensitive inner skin of the windpipe (tracheal mucosa). It is a common observation that the tip of the small catheter strikes against the inner wall of trachea as a consequence of the respiratory movement. In addition to this mechanical trauma, the surrounding tissue is dried out by the high flow oxygen stream.

Furthermore, so-called "Montgomery T-tubes" can be inserted into the trachea and a patient can obtain oxygen via a shank of the T-piece external to the patient. In needed, the patient can draw off secretions using a suction catheter and a vacuum pump. The patient can breathe freely and speak when the front shank is closed; however, normal artificial positive pressure ventilation is not possible via the Montgomery T-tube since the introduced air escapes upward into the oral cavity or the pharyngeal area. An additional limitation of the above-referenced therapies is the impaired mobility of the patient because of inadequate ventilation or because of the bulk of the apparatuses.

Jet ventilators are state of the art, but these devices are not synchronized with a patient's breathing. On the other hand, invasive ventilators with cuffed tubes are synchronized because there is a direct feedback of the pressure inside the inflated lung to the sensors inside the respirator. However, there are no respiratory systems that use feedback from sensors in the body to properly synchronize and control the ventilator.

Whether the breathing disorder is COPD/emphysema, fibrosis, sleep apnea, or otherwise, difficult breathing is a serious, often life-threatening problem. Therefore, there is an existing need for a respiratory system that provides a more efficient method for supporting the respiration of a patient that can be used to treat many disorders, are minimally invasive, mobile and taken along by the patient, and/or reliable in use. Moreover, there is a need for respiratory support systems that simulate the patient's spontaneous respiration without adversely affecting the patient's ability to speak. Additionally, there is a need for a respiratory support system capable of using pressure or flow signals from inside the body to properly synchronize and control a ventilator.

SUMMARY OF EXEMPLARY EMBODIMENTS

The invention includes systems, methods, and apparatuses that improve the quality of life for patients that require respiratory support. These respiratory systems, methods, and apparatuses can provide a more efficient way of supporting the respiration of a patient by providing additional oxygen when needed in accordance with the principles of the invention.

In one embodiment, a tracheal prosthesis and a catheter in accordance with the principles of the invention can provide for respiratory support that can be synchronized with the spontaneous respiration of the patient and still allow the patient to speak.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE FIGURES

The accompanying drawings, which are included to provide a further understanding of the invention, are incorporated in and constitute a part of this specification, illustrate preferred embodiments of the invention and together with the detailed description serve to explain the principles of the invention.

In the drawings:

FIG. 17 shows an embodiment of a dual lumen catheter in accordance with the invention.

FIG. 18 shows an embodiment of the flow through the catheter of FIG. 17 during inspiration in accordance with the principles of the invention.

FIG. 19 shows an embodiment of the flow through the catheter of FIG. 17 during expiration in accordance with the principles of the invention.

FIG. 20 shows an embodiment of a dual lumen catheter having a gliding wall in accordance with the invention.

FIG. 21 shows the catheter of FIG. 20 with the gliding wall in a different position.

FIG. 22 shows an expanded view of an air outlet of the catheter in FIG. 20.

FIG. 23 shows an expanded view of an air outlet of the catheter in FIG. 21.

DETAILED DESCRIPTION OF PREFERRED EMBODIMENTS

The present invention, in a preferred embodiment, provides systems, methods, and apparatus for supporting the respiration of a patient. This can be accomplished by providing controlled synchronized ventilation with a directed flow of an oxygen-bearing gas. The oxygen-bearing gas may be substantially pure oxygen, mixtures of oxygen and nitrogen, mixtures of oxygen and inert gases, ambient air, or various combinations thereof. In addition, the oxygen-bearing gas may include fragrances, aerosolized drugs, humidification or heating. The oxygen-bearing gas can be provided as needed upon inhalation and/or expiration, preferably, based upon sensing of the patient's spontaneous breathing.

By providing a jet boost of an oxygen-bearing gas upon inspiration, as needed, the patient can inhale more oxygen. Preferably, the additional oxygen is administered at the end of inhalation, in particular, after the peak of inspiratory flow is detected. The administration of additional oxygen can improve the depth of ventilation during inhalation. However, the additional oxygen may be administered at any point during inhalation. Additionally, a countercurrent or counter pulse during expiration can be delivered, which creates a back-pressure in the airways similar to the pursed lips breathing strategy applied by physiotherapists in order to avoid a collapse of the respiration paths. By providing an oxygen-bearing gas upon expiration through counter pulses (e.g. bursts or pulses of oxygen-bearing gas directed against the direction of the flow during expiration), a dynamic collapse of the airways can be minimized or prevented, over inflation of the lung can be minimized, and clearance of carbon dioxide from the lungs can be improved. Therefore, in accordance with the principles of the invention, whether used for inhalation and/or exhalation, breathing requires less energy and the patient's pain, dyspnea and exhaustion are relieved. Moreover, the systems and methods of the invention can be used for treatment of many breathing disorders, including, but not limited to, COPD, emphysema, fibrosis, and sleep apnea.

Figure 1:
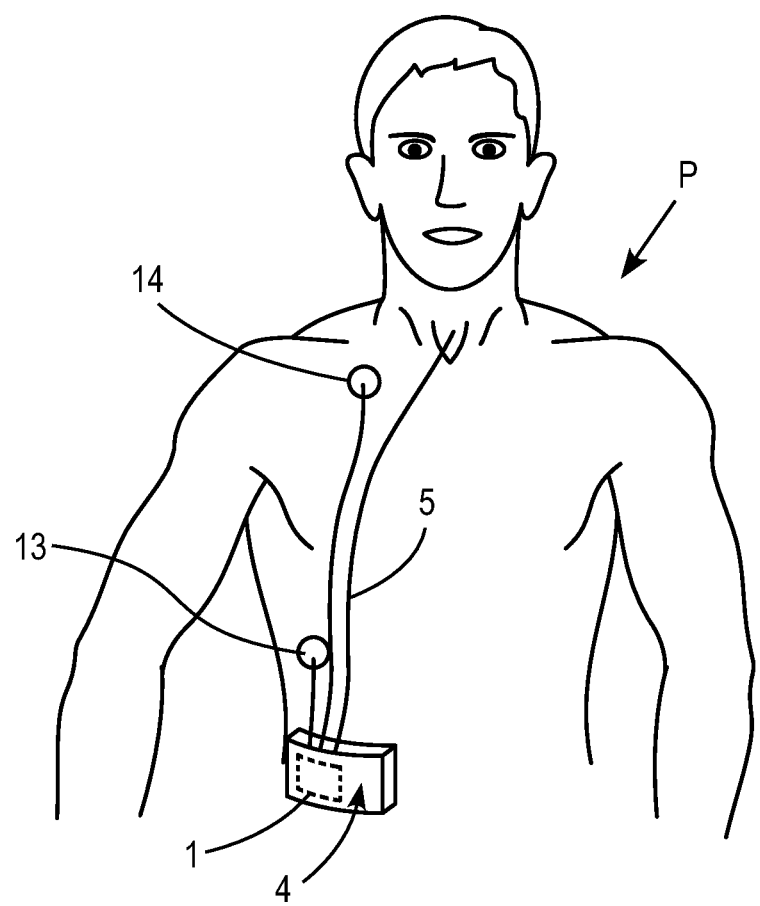
FIG. 1 shows the upper body of a patient carrying an embodiment of a system for respiration support in accordance with the principles of the invention.

Referring to FIG. 1, in accordance with one embodiment of the invention, patient P designates a patient suffering from a breathing disorder, for example, pulmonary emphysema, with overloading and exhaustion of the respiratory muscles. As a consequence, the patient cannot inhale enough oxygen because the lungs are compromised. In addition, the patient cannot exhale enough carbon dioxide because the patient has slack and collapsing respiratory paths. The system of FIG. 1 generally includes the ability to detect the patient's spontaneous respiration and the ability to provide oxygen to the lungs of the patient during spontaneous inspiration and/or exhalation.

Figure 13:
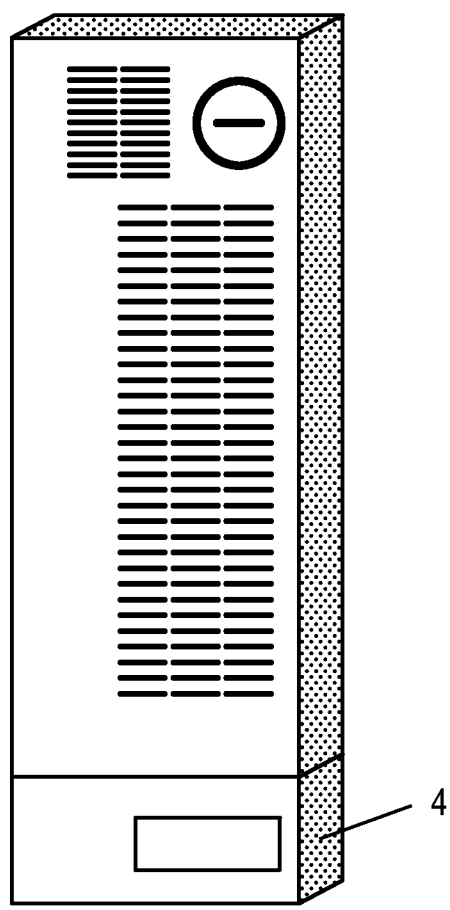
FIG. 13 shows a system in accordance with an embodiment of the invention where the pump and control unit are integrated with the oxygen tank.
Figure 25:
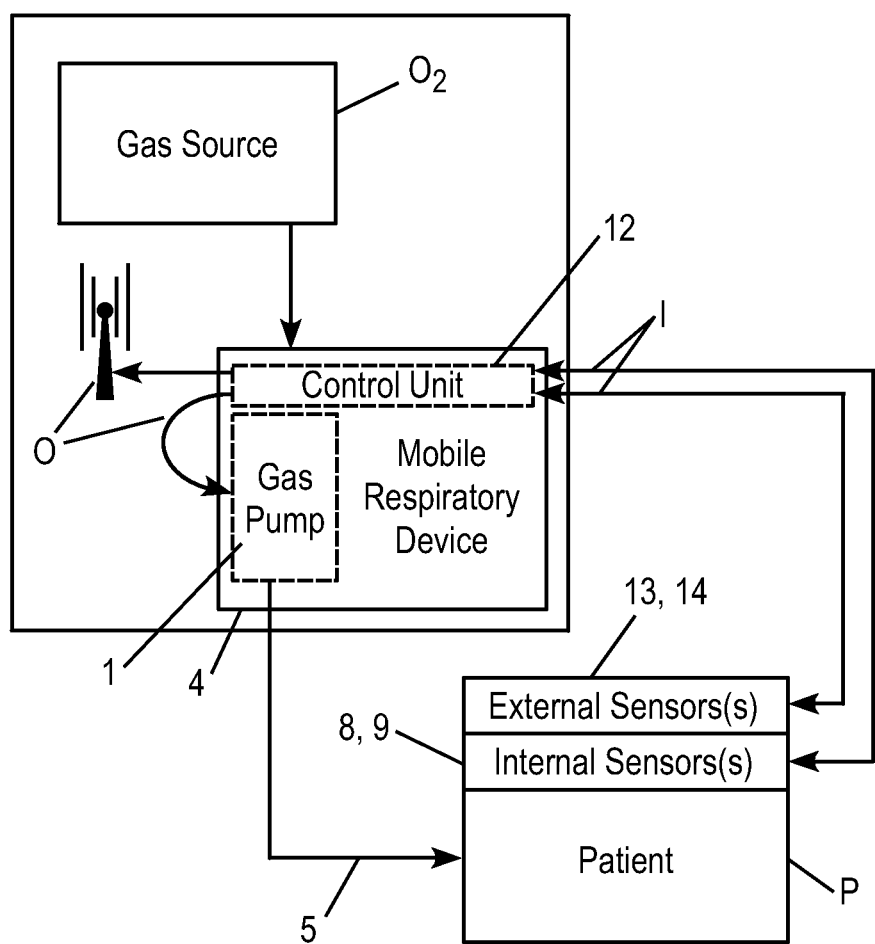
FIG. 25 is a diagram of the overall system.

As shown, the respiration support of patient P in accordance with the principles of the invention can be implemented in a system, method, or apparatus that may be compact and/or portable. Other systems are contemplated including, for example, providing for use with a ventilator or oxygen source as shown in FIG. 13. The overall system of the invention is described in FIG. 25, indicating the gas source O2, the pump apparatus 1 and control system 12, the catheter 5 and internal sensors 8, 9 and the patient P. The gas source O2, pump apparatus 1 and control system 12 can be separate or integrated components of the system. The control unit 12 may be connected I to internal sensors 8, 9 and/or external sensors 13, 14.

In accordance with the embodiment of FIG. 1, in general, patient P's spontaneous breathing can be detected by way of sensors. A catheter 5 can be used to introduce oxygen into the lungs as needed. The sensors and catheter can be associated with the patient in a variety of ways. As illustrated in FIG. 1, a catheter 5 is introduced in the trachea. Also, a catheter 5 could be introduced at other points into a patient P, including, for example, through the mouth or nose of the patient P, or accessed into the trachea by an artificially created entry point somewhere on the body and tunneled internally to and into the trachea. The catheter 5 can be secured in the trachea in a variety of ways. In one embodiment, the catheter 5 can be associated with a tracheal prosthesis as discussed later or using a positioning catheter as also discussed later with reference to FIGS. 3 and 4, for example.

Figure 2:
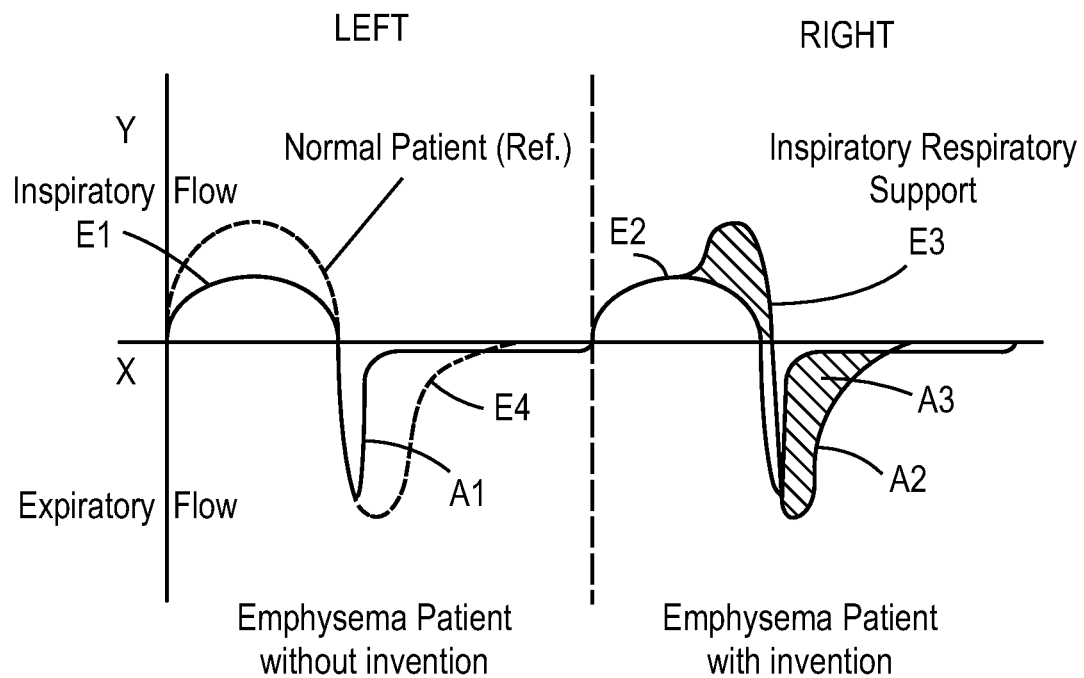
FIG. 2 shows a diagram with a view of the respiration flow of an emphysema patient without respiration support and with respiration support in accordance with the principles of the invention.

The system of FIG. 1 generally includes an oxygen-bearing gas source (not shown), gas pump 1, mobile respiratory device 4, a set of exterior sensors 13, 14, and a set of interior sensors (not shown) disposed inside the trachea of the patient P. The oxygen-bearing gas pump 1 can be connected to a gas source (see FIG. 5) and catheter 5 to introduce an oxygen-bearing gas into the patient's lungs by way of the trachea, as shown, although other entry points can be used in accordance with the principles of the invention as discussed above. According to FIG. 1, the oxygen-bearing gas pump 1 is shown as a component of a compact, easily portable respiration device 4. The device 4 could alternatively be housed in a component with a gas tank or oxygen-bearing gas source as illustrated in FIG. 13. With the sensors in accordance with the principles of the invention, the spontaneous respiration of the patient can be detected. Typically, the information from the sensors is communicated to the gas pump 1. However, the information from the sensors may also be communicated to a cellular telephone or other wireless systems that can communicate information to a healthcare provider/hospital, etc., for 24-hour monitoring and response from the healthcare provider/hospital, etc. The patient then can receive a pressure boost of oxygen-bearing gas as needed in accordance with the principles of the invention. FIG. 2 illustrates both spontaneous respiration of the patient P without the invention (right) and respiration supported in accordance with the principles of the invention (left). The x-axis in this diagram represents time and the y-axis represents the amount of flow (change in volume over time) of oxygen-bearing gas, which can be liters per second or any other appropriate measurements. The spontaneous respiration process with inspiratory flow and expiratory flow without respiratory support for patient P is shown in the left half of FIG. 2. The curve for inhalation is designated by E1 and the curve for exhalation by A1. As illustrated by curve E1, during inhalation the tidal volume inhaled is reduced from that of a normal patient. For example, a patient with emphysema with flattened diaphragms or a patient with stiff lungs suffering from fibrosis cannot breathe in enough air (oxygen) in one breath. Both patients typically experience shallow breathing. Therefore, the patient requires more breathing cycles to get the requisite amount of oxygen and clear carbon dioxide. During exhalation, as illustrated by curve A1, the expiratory flow of the emphysema patient is reduced because the respiratory paths can be slack and tend to collapse before an adequate amount of carbon dioxide is expelled from the lungs.

The sensors allow the patient P's breathing to be monitored continuously so that a jet flow of oxygen-bearing gas can be supplied in accordance with the principles of the invention, that is, when a deeper breath is needed. In particular, at the end of an inhalation process of the lungs, an additional volume (oxygen) can be administered to patient P, as discussed in more detail below. This respiratory flow is illustrated in the right half of FIG. 2. As illustrated, an additional amount of oxygen-bearing gas provided to patient P increases the respiratory volume during inhalation according to curve E2 by the volume difference shown darkened in the upper curve and designated by E3. The additional amount of oxygen-bearing gas can have an extra space tidal volume between 25 ml and 150 ml.

In addition, the exhalation process of the patient can be braked or slowed by a countercurrent. As a consequence thereof, the respiratory flow shifts during exhalation along the curve designated by A2. This purposeful resistance acting opposite to the exhalation prevents a collapsing of the respiratory paths during exhalation. In this manner, the exhalation volume can be increased by the volume also shown darkened and designated by A3. The amount of carbon dioxide that is exhaled can be increased by a statistically significant amount. The amount of carbon dioxide that is exhaled can be increased by at least 5%. Preferably, the amount of carbon dioxide exhaled is increased from 5% to 30%. More preferably, the amount of carbon dioxide exhaled is increased about 20% to 30%.

As a consequence, the invention may avoid insufficient respiration from an undersupply of oxygen and an increase of carbon dioxide in the blood. The patient P may be significantly less stressed and more mobile, and may perceive less or no shortage of air.

The sensors for detecting and monitoring respiration will now be discussed in more detail. To detect spontaneous respiration of the patient P, sensors can be associated with an end of the catheter that is disposed in the trachea of the patient P. In one embodiment, the invention can include connecting the catheter to a tracheal prosthesis (e.g. FIGS. 3, 4, and 7) or can include a catheter-positioning device (e.g. FIGS. 14, 15, and 16A-16E) to more reliably and accurately direct the oxygen flow into the patient's airways and away from a tracheal wall. Preferably, in accordance with the principles of the invention, oxygen is introduced into the patient P in such a manner that the patient P can freely breathe and speak without restriction.

Figures 3, 4:
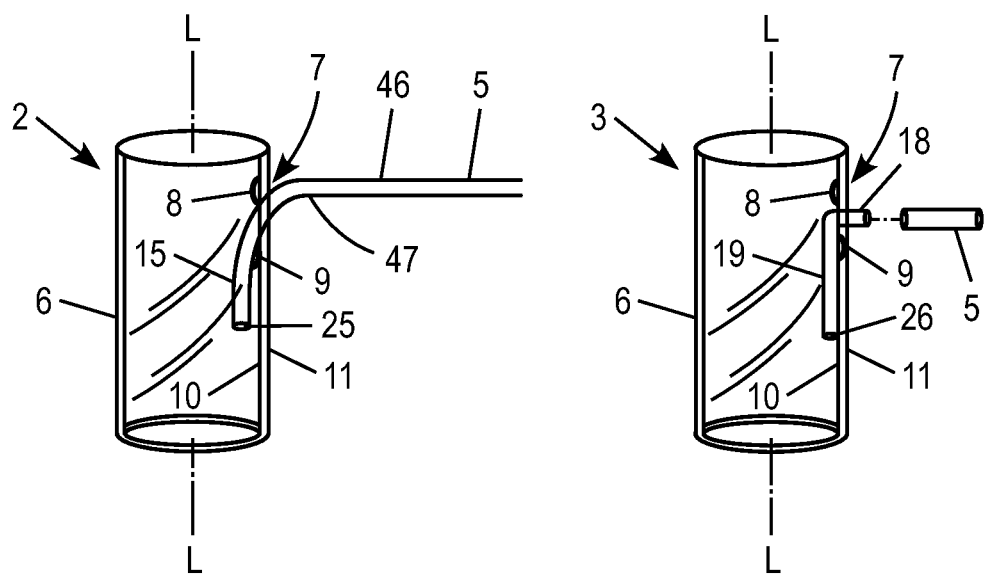
FIG. 3 shows a technically simplified view of an embodiment of a tracheal prosthesis in accordance with the principles of the invention.
FIG. 4 shows another embodiment of a tracheal prosthesis in accordance with the principles of the invention.
Figure 5:
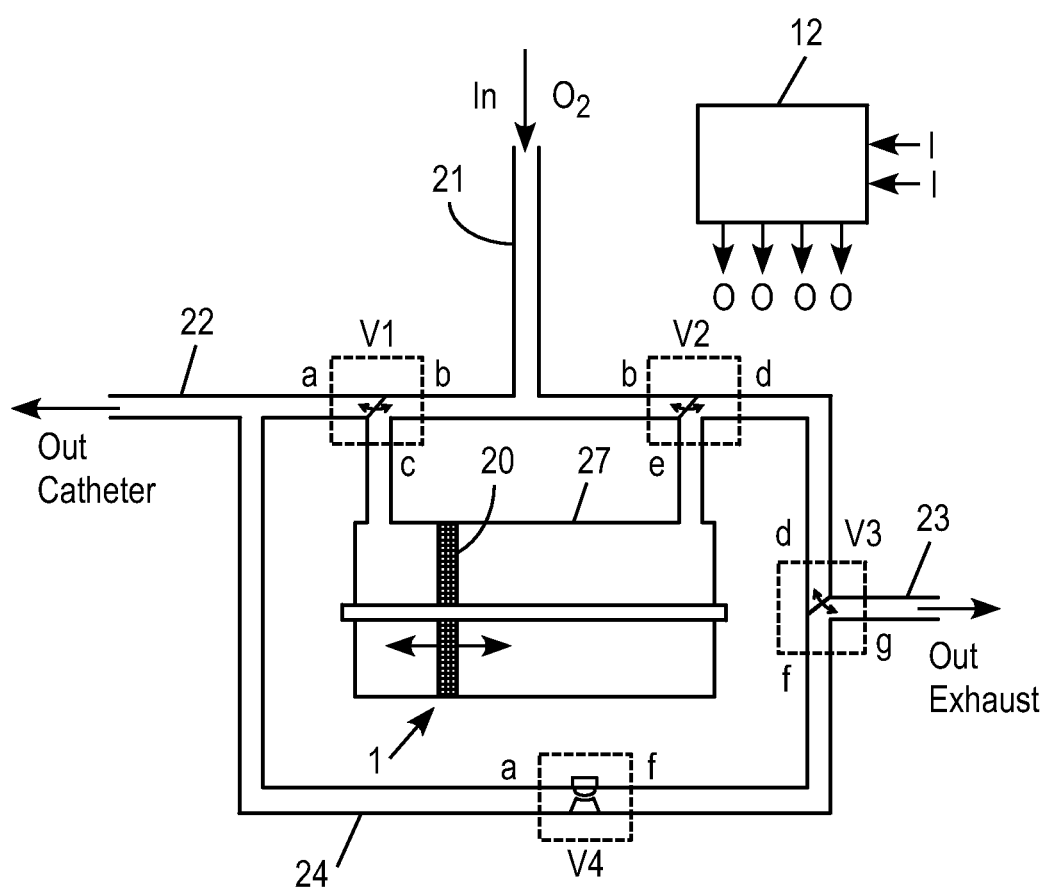
FIG. 5 shows a schematic of an embodiment of an oxygen-bearing gas tank and pump showing the conduction of air and a control unit in accordance with the principles of the invention.

In one embodiment, as shown in FIGS. 3 and 4, the sensors can be disposed on a tracheal prosthesis 2, 3. Each tracheal prosthesis 2, 3 is shown having a tubular support body 6 with a connection 7 for a catheter 5. As shown, two sensors 8, 9 detect spontaneous respiration of the patient P, and can be associated with a support body 6. The sensors 8, 9 can be thermistors, that is, temperature dependent resistors. The sensors 8, 9 can detect tracheal flow of the patient because inspired air and expired air have different temperatures. The thermistors 8, 9 can be connected together in a bridge circuit in the apparatus to compensate for changes in ambient air temperature. Other types of sensors can be used in accordance with the principles of the invention including, for example, a pressure sensor as discussed later. Both sensors 8, 9 can be located on an inner wall 10 of the support body 6 (FIG. 3), or one sensor 8 can be fixed on the inner wall 10 of the support body 6 and the other sensor 9 can be located on an outer wall 11 of the support body 6 (FIG. 4). The sensors 8, 9 communicate with a control unit 12 for activating an oxygen jet pump 1. The sensors 8, 9 can be connected by wires or by wireless communication. The control unit 12 can be any type of microprocessor that is capable of processing the collected data in accordance with the invention. The control unit 12 is schematically shown in FIG. 5 with its inputs (I) and outputs (O). The inputs (I) represent information coming from the sensors. The outputs (O) represent information that is used to control the pump 1.

In the tracheal prosthesis 2 according to FIG. 3, the jet catheter 5 can be inserted via connection 7 into the support body 6. An end 15 of jet catheter 5, located in support body 6, is preferably guided or deflected approximately parallel to its longitudinal axis L. The data lines from sensors 8, 9 to the control unit 12 run inside the catheter 5. The invention is not limited to data lines; transmission from sensors can be any type of transmission, including wireless. On the discharge side, the end 15 of the jet catheter 5 is preferably designed as a jet nozzle 25. The jet nozzle 25 increases the speed of an oxygen current being discharged from the catheter 5, and the current is conducted in the direction of the bronchial tract. The diameter of the support body 6 is dimensioned with a sufficiently free lumen in such a manner that the patient P can freely breathe and speak even with the integrated catheter 5.

In another embodiment, a separate coupling 18 is provided on the connection 7 in the tracheal prosthesis 3 according to FIG. 4. The catheter 5 can be connected to the tracheal prosthesis 3 with the separate coupling 18. In this instance, a fixed longitudinal section 19 aligned parallel to the longitudinal axis L can serve as the catheter end in the support body 6, and the oxygen current is conducted via a jet nozzle 26 in the direction of the bronchial tract.

The tracheal prosthesis, when used, can comprise various configurations, shapes and dimensions. For example, the tube could be T-shaped or L-shaped or otherwise. The size, shape, and/or cross-section can vary, for example, to accommodate removal or to direct the catheter. The tracheal prosthesis could be a portion of a tube having, for example, a semi circular cross-section. Furthermore, expandable and self-expandable prongs or petals can be used at the tracheal opening to secure the prosthesis in place. In one embodiment, the prosthesis can include a tubular member with a tracheal side opening including prongs or petals surrounding, in whole or in part, the access hole. The prongs or petals may function like a rivet in the neck opening. The tracheal prosthesis can also be coated to avoid mucus retention, prevent the formation of granulation tissue, or can act as a drug-releasing device. The tracheal prosthesis may also include other coatings, such as lubricious coatings and hydrogel anesthetics. Thus, the tracheal prosthesis can serve as a guide for the catheter, to hold sensing devices, serve as a drug delivery device, and/or to minimize mucus plugs that can form on the catheter tip.

In addition to internal sensors, external sensors can be provided. FIG. 1 also shows respiration sensors 13, 14, preferably, impedance electrodes or respibands. Signals from the sensors 13, 14 are also for detecting the spontaneous respiratory efforts of the patient P. An exact image of the respiration process of patient P can be obtained by processing the measured values received via sensors 8, 9 and 13, 14. In addition, the safety against false measurements or the failure of one of sensors 8, 9 and/or 13, 14 can be increased due to redundancy.

Although the sensors are shown in certain locations on the patient P, other locations that would allow the sensor to sense the patient's respiration, directly or indirectly, can be used. For example, sensors can be provided on the catheter as discussed later. Alternatively, a pill-type sensor or nano device can be used and/or implanted to communicate by, for example, wireless transmission to communicate with the control unit to operate the oxygen flow through the catheter in accordance with the principles of the invention.

Figure 6:
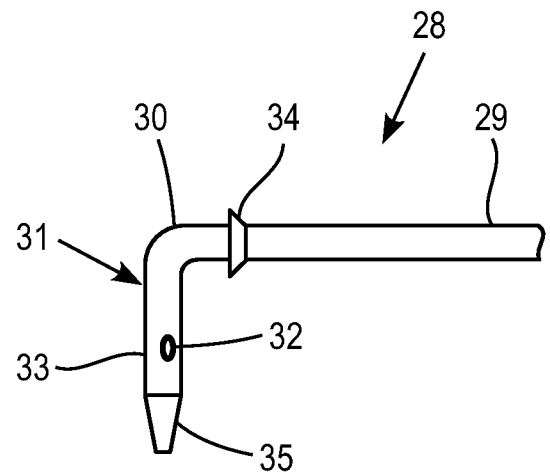
FIG. 6 shows an embodiment of the end section of a catheter in accordance with the principles of the invention.
Figure 7:
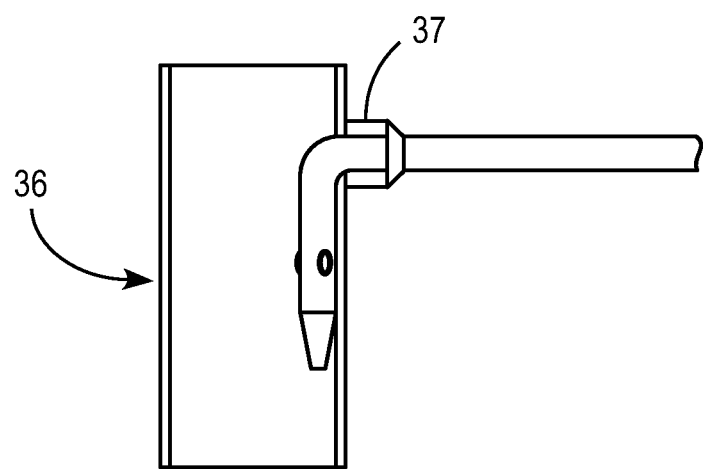
FIG. 7 shows the catheter according to FIG. 6 inserted in a support body in accordance with the principles of the invention.

One embodiment where sensors are provided on the catheter is shown in FIG. 6. FIG. 6 shows a catheter 28 with a long, flexible tube 29 and an end 31 on the discharge side bent in a curvature 30. The catheter 28 can be pre-formed to provide a desired curvature 30. With the appropriate curvature 30, the catheter 28 can be entered into the trachea with or without use of a prosthesis. In this embodiment, two sensors 32, 33 for detecting the spontaneous respiration of the patient P can be fastened on the end of the catheter 28. The sensors 32, 33 are preferably thermistors, but as in all embodiments herein, could be other types of sensors. Furthermore, in other embodiments of the invention, additional sensors may be used. In still other embodiments of the invention, fewer sensors may be used. Data lines are not shown in the drawing for the sake of simplicity and could include any form of data transmission. In a hard-wired embodiment, data lines can run through the catheter 28. A catheter flange 34 designates a stop for use with a support body 36, as shown in FIG. 7. It can also be seen that an end 31 of the catheter 28 is provided with a jet nozzle 35. The cross-section of gas flow is reduced relative to the cross-section of the catheter 28 in the jet nozzle 35 so that the discharge rate of the supplied oxygen is increased.

The catheter 28 can be introduced into the support body 36, as shown in FIG. 7. The support body 36 is located in the trachea of the patient P. A connection to the outside is established via a connection 37. In the body, the tip or jet nozzle end 35 of the catheter 28 can be disposed in the trachea. Preferably, the tip of the catheter 28 does not touch the tracheal wall. The support body 36 can be a traditional Montgomery T-stent.

Figure 8A:
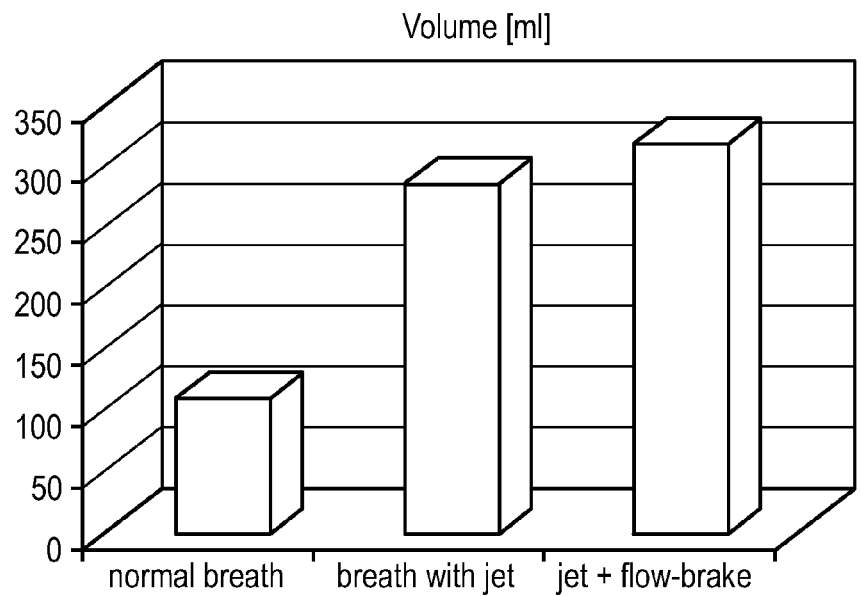
FIGS. 8A and 8B show graphs of breathing data generated from a bench model test in accordance with the principles of the invention.
Figure 8B:
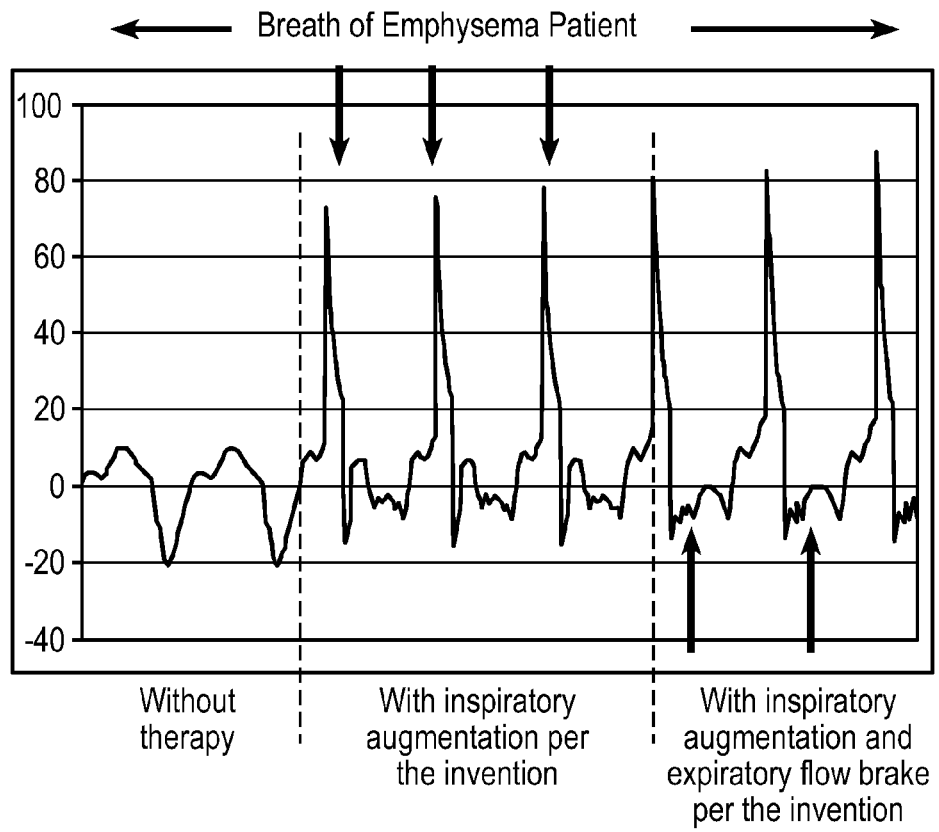

FIGS. 8A and 8B show measurements in a lung model emulating respiratory diseases. FIGS. 8A and 8B graphically illustrate an increased tidal volume with the invention. FIG. 8A shows a bar graph of the volume (ml) of breath comparing a pathologically low breath of a patient with emphysema at about 90 ml; the volume with jet oxygen in accordance with the principles of the invention upon inhalation at about 260 ml; and the volume with the jet oxygen in accordance with the principles of the invention upon inhalation and with the flow brake (oxygen jet) upon exhalation at about 300 ml. FIG. 8B shows a graph of the flow of breath (liters per second) over time for a breath of an emphysema patient; the flow with jet oxygen in accordance with the principles of the invention upon inhalation; and the flow with jet oxygen in accordance with the principles of the invention upon inhalation and with the flow brake (oxygen jet) upon exhalation.

Figure 10:
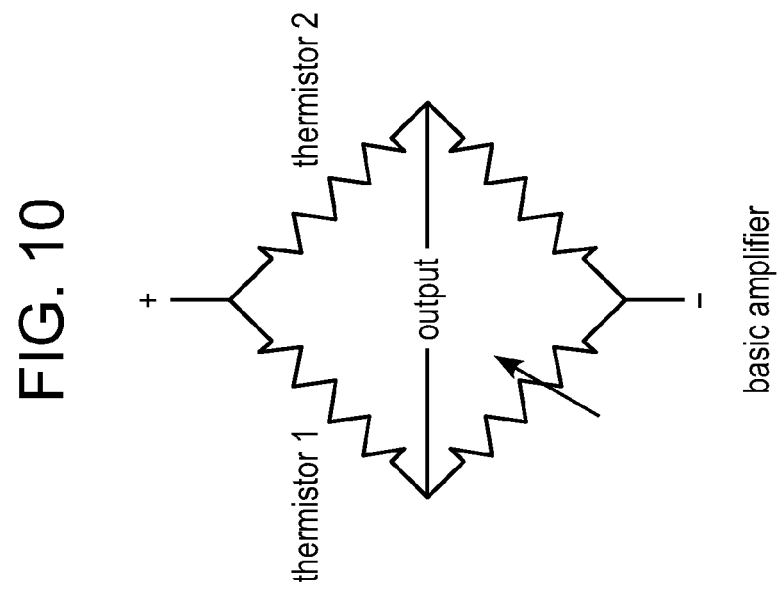
FIG. 10 shows a schematic of an embodiment of a circuit in accordance with the invention.
Figure 9:
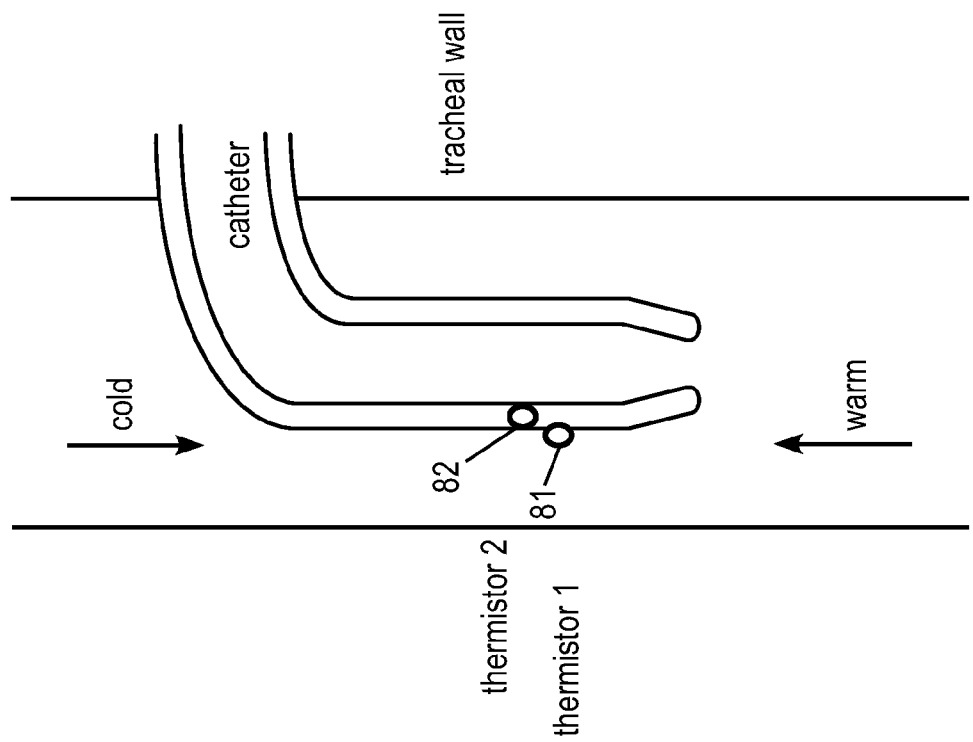
FIG. 9 shows an embodiment of a catheter and sensors in accordance with the invention.

In another embodiment shown in FIGS. 9 and 10, thermistors 81 and 82 can be provided on a catheter tip inside the trachea. The thermistor 81 is more exposed to the gas stream than thermistor 82, which is protected against fast temperature changes because it is inside the catheter wall (or under a protection film). Alternatively, multiple thermistors with different response times could be used. Over a longer period (e.g. 10 seconds), both mean temperatures will be the same (equilibrium) and the bridge (FIG. 10) will be readjusted. This compensates for changes in ambient temperature, fever, etc. Rapid changes based upon breathing in colder air and breathing out warmer air is detected by the thermistor 81. The output signal is sent through a differentiator. The peaks of the thermistor signal match the highest flow rates. The minimum in the differentiated signal matches the peak of the inspiratory flow and the peak of the expiratory flow. Undifferentiated and differentiated signals are fed into the microprocessor. One way to determine peak inspiratory flow (trigger for beginning introduction of oxygen) would be to look for minimum in absolute temperature (cold air comes in) and zero change of temperature (differentiated signal is zero). The advantage of using the above multiple thermistor approach is that the difference between the signals from the two thermistors cancels out flow artifacts found in the measured respiratory flow pattern, such as would be caused by vibration or other anticipated events, and to compensate for drift in the thermistor signal such as would be caused by changing external or internal temperature or humidity conditions.

Figure 12:
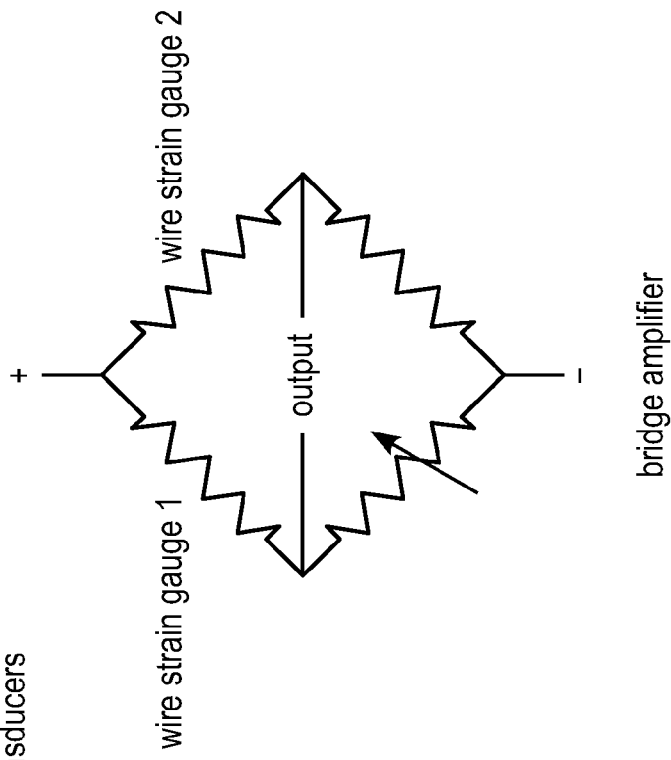
FIG. 12 shows a schematic of another circuit in accordance with the invention.
Figure 11:
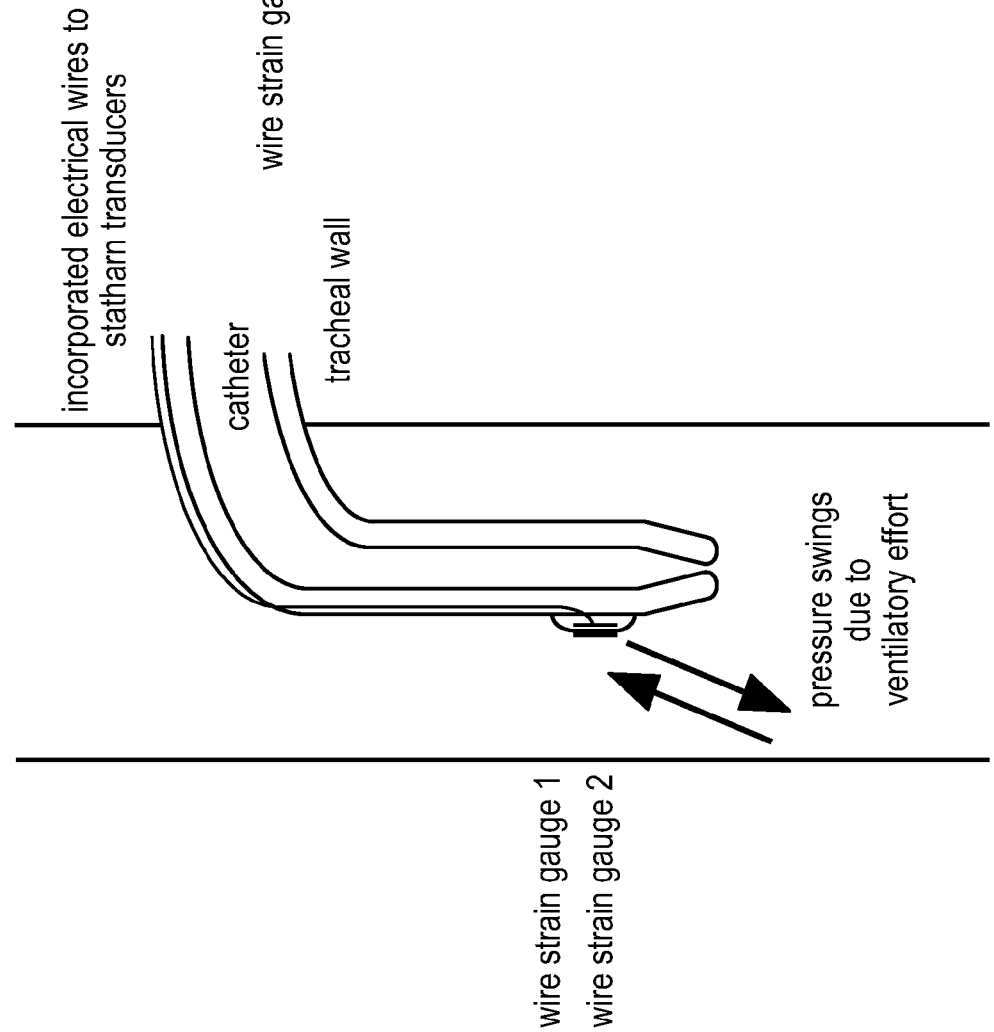
FIG. 11 shows another embodiment of a catheter and sensors in accordance with the invention.

In another embodiment, as shown in FIGS. 11 and 12, FIG. 11 shows a pressure transducer that is a modified silicone wire strain gauge element 90. Instead of a typical silicone membrane, the wall of the catheter is used. If the wall of the catheter deforms under the pressure swings inside the trachea (breathing effort), then an electrical signal from the bridge amplifier is fed into a microprocessor. This embodiment can be used alternatively to the thermistors, as a redundant signal or as a back-up signal. Other sensors could be semiconductor flow sensors or pressure sensors. FIG. 12 shows a circuit diagram of a bridge amplifier.

Other sensors can be used in accordance with the invention. For example, sensors and/or secondary control sensors could be: respibands (chest wall strain gages), respitrace signals (conductance plethysmographs), pressure sensors inside or outside the body, transthoracic electrical impedance measuring devices, flow sensors at the mouth or nose (pneumotachographs), and/or capnometers (carbon-dioxide sensors). Moreover, the sensors in accordance with the invention can communicate data or information to the control unit by any devices, mechanisms, or methods. For example, communication can occur by way of wire, wireless, or remote transmission. The advantage of using non-thermistor sensors is that the thermistor approach may have the disadvantage of the thermistor head collecting airway mucus, which could be corrected for in a variety of ways such as with cleaning. However, other non-thermistor sensors may be less susceptible to annoyances like mucus collection. Further, with thermistor sensors, inevitable changes in ambient temperature, while compensatable in the thermistor signal processing algorithms, are potentially problematic to system reliability. Therefore, the other types of sensors stated above may be advantageous over thermistor sensors, or in addition to the thermistor sensors.

In addition to measuring the respiration pattern, it is often desirable to measure airway pressure for safety reasons, for which thermistor sensors may not be the best approach. Therefore, some of the sensors mentioned above can also be used as a safety control device. For example, pressure sensors can be used to sense the inspiration of the patient (like the thermistors), but they can also be used to sense a high pressure in the trachea and shut off the jet machine in order to prevent baro-trauma (damage from high pressure).

An oxygen-bearing gas is provided on demand by the gas pump 1. The gas pump 1 is schematically shown in FIG. 5. The gas pump 1 can be a piston pump with a double-acting piston 20 arranged in a cylinder 27. The piston pump of the present embodiment comprises four valves V1 to V4. Other piston pumps (not shown) may have greater than or fewer than four valves. The supply of oxygen emanates from an external oxygen reservoir via a connection 21. The switching states of valves V1 to V4 and the supply lines and removal lines are designated by letters a to g. Other types of pumps can be used in accordance with the principles of the invention.

The gas pump 1 functions in the apparatus during the support of respiration as follows. When valve V1 is open from c to a (b to c closed) and valve V2 is open from b to e (e to d closed), piston 20 moves to the left in the plane of the figure and the oxygen flows via outlet 22 and jet catheter 5 to the patient P. An additional amount of oxygen E3 is administered during the inhalation process of the patient P.

When valve V1 is open from b to c (c to a closed) and valve V2 is open from e to d (b to e closed), piston 20 moves to the right in the plane of the figure and the flow of oxygen takes place in the direction of valve V3. Valve V3 is connected to the ambient air via an outlet 23. In the instance in which valve V3 is open from d to g, the oxygen flows off without expiration brake. That means that the exhalation process is not braked by a countercurrent.

If valve V3 is closed from d to g and open from d to f, the oxygen flows via access path 24 in the direction of the outlet 22 and the catheter 5 in order to be administered to the patient P during the exhalation process and in order to break the respiratory flow. The countercurrent prevents a collapsing of the respiratory paths and keeps them open, making a deeper exhalation possible.

Furthermore, valve V4 is located in access path 24 of the apparatus, via which the flow through (f to a) can be variably adjusted. This advantageously can be a proportional valve with pulse-width modulation.

As discussed above, the catheter preferably includes a jet nozzle. Any type of jet nozzle can be used to achieve the necessary jet flow. The jet flow speed in accordance with the invention can be significantly higher than 100 m/s. By comparison, the speed through a conventional ventilator tube or mask is significantly lower than 100 m/s. When the jet flow rate is high enough, there is enough speed so that directed flow is accomplished and no sealing tube cuff would be necessary. Under normal ventilation, the volumetric inspiratory flow rate is in the range of about 500 m$^3$ to 1000 cm$^3$ in 2 seconds. A peak inspiratory flow maximum can be 1000 cm$^3$/second. In the case of normal invasive ventilation, the flow of 1000 cm$^3$/s (peak) goes through a tube of approximately 8 mm diameter. The speed of this gas stream, determined by dividing the volumetric inspiratory flow rate by the area of the tube, is 1000 cm$^3$/(0.4)$^2$ cm$^2$*Pi=2000 cm/s=20 m/s. During jet ventilation, approximately half of this flow goes through a jet cannula of 1.5 mm diameter. As the flow profile is rectangular, the peak flow rate is 500 cm$^3$/s. Therefore, the speed of the jet gas stream is 500 cm$^3$/(0.075)$^2$ cm$^2$*Pi=28313 cm/s=283 m/s. In accordance with a preferred embodiment of the invention, 100 ml (cm$^3$) are pressed through a catheter of approx 1.5 mm diameter in half a second. Preferably, the peak flow for this embodiment is 100 cm$^3$ in 0.25 seconds=400 cm$^3$/s. The speed of this gas stream is 400 cm$^3$/(0.075)$^2$ cm$^2$*Pi=22650 cm/s=226 m/s. In other preferred embodiments, the speed of the gas stream is from approximately 100 m/s to approximately 300 m/s. Preferably, the speed of the gas stream is from approximately 200 m/s to approximately 300 m/s. Preferably, the speed of the gas stream is from approximately 250 m/s to approximately 300 m/s.

Figure 14:
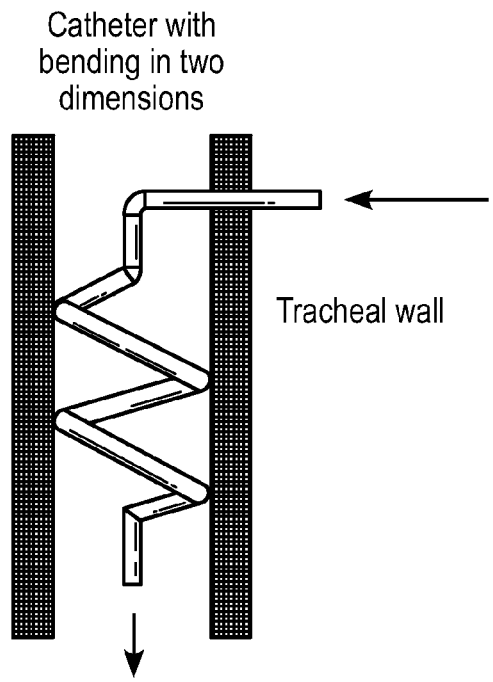
FIG. 14 shows an embodiment of a distal end of a catheter in accordance with the invention.
Figure 15:
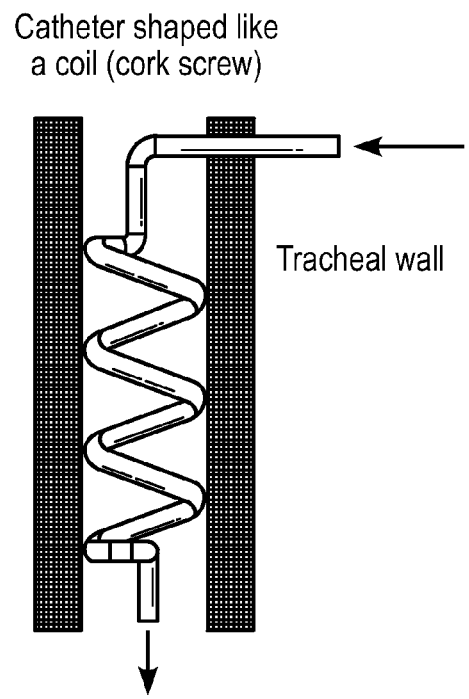
FIG. 15 shows another embodiment of a distal end of a catheter in accordance with the invention.
Figure 16A:
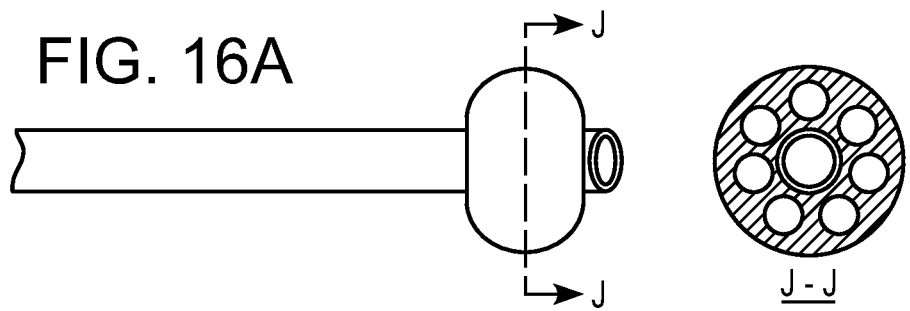
FIGS. 16A-16E shows embodiments of a catheter in accordance with the invention.
Figure 16B:
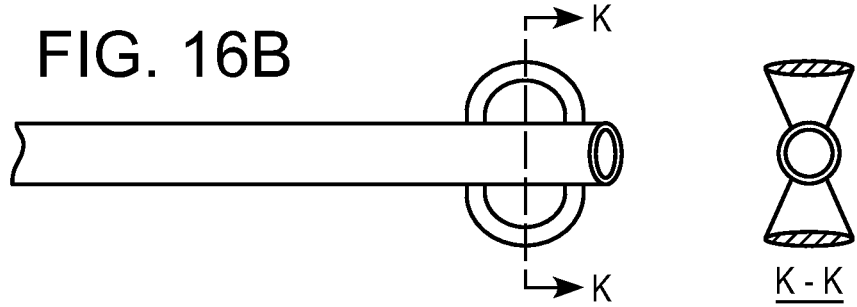
Figure 16C:
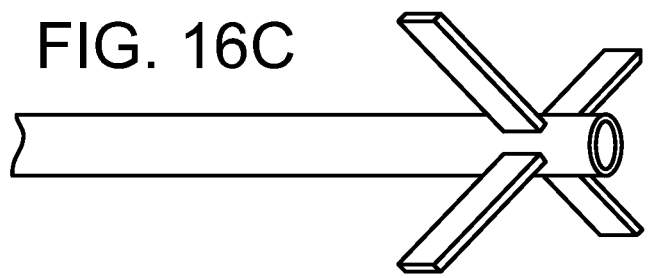
Figure 16D:
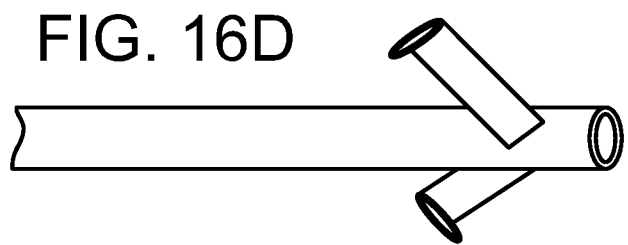
Figure 16E:
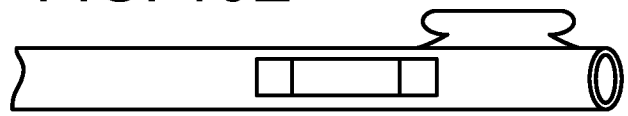

When the tip of the catheter touches the wall of the trachea, there is a potential risk of tissue damage. The catheter tip or the high flow gas stream can harm the mucosa. To efficiently and effectively direct the air inside the body, the catheter can be configured to provide a directed flow of oxygen. In particular, the catheter is preferably configured so that the exit of air from the catheter output end can expel and direct air down the center of the trachea to avoid directing the jet flow of oxygen against the tracheal wall. Also, the catheter tips are preferably configured to minimize venturi and the mucus formation proximal to the venturi on the outer wall of the catheter. A shielding Montgomery T-tube as described above can be used to overcome that problem. In FIGS. 14 and 15, the catheters are configured such that the catheter tip or jet nozzle avoids contact with the wall of the airway; the tip is substantially centered in the trachea. This can be accomplished by configuring the catheter so that the catheter will contact the tracheal wall at several locations to distribute the local pressure, and the tip where the jet flow of oxygen exits the catheter is substantially centered in the trachea. Accordingly, the use of a tracheal prosthesis is not necessary. One way to avoid the contact between the tip (jet nozzle) and the airway wall is to bend the catheter like a zigzag in two planes as illustrated in FIG. 14. Another embodiment is a corkscrew as illustrated in FIG. 15.

FIGS. 16A-16E shows alternate embodiments for centering the catheter where balloons (FIGS. 16A and 16B) or clips (FIG. 16C-16E) can be used to center the catheter tip. Preferably, the clips are made of a resilient material.

Referring now to FIGS. 17-23, a dual lumen catheter will be described. The invention can also include the ability to better distribute the directed flow (FIGS. 17-19) and/or change the direction of the flow (FIGS. 20-23). FIGS. 17-19 show a dual lumen catheter 172. The catheter tip, shown generally at 170, is disposed in a trachea 174. The catheter 172 has two lumens, formed by inner cannula 176 and outer cannula 178. Inner cannula 176 directs flow to a catheter nozzle 180, as discussed above. As shown in FIG. 18, upon inspiration, inspired flow is enhanced by air entrainment from the jet flow through the inner cannula plus by the additional jet flow itself 176. Upon expiration (FIG. 19), exhaled flow is enhanced by turbulence from counter flow through ports 182 by means of propping the respiratory paths open. The ports 182 need not be of any particular shape and may be, for example, circular, hexagonal, oval, or slits. Although not shown, turbulent flow could also be provided through inner cannula 176 during exhalation to enhance exhaled flow depending upon the desired effect.

Referring to FIGS. 20-23, another embodiment of a catheter is shown. A catheter 200 is shown with a distal tip 202 in a trachea 204. The catheter tip 202 includes a cannula configuration with an inner lumen 206, an outer lumen 208 concentric to the inner lumen, and a gliding sheath 210. In this embodiment, the gliding sheath 210 moves relative to the cannula to allow ports 210 to change the direction of oxygen flow as illustrated in FIG. 20 verses FIG. 21, and in close-up in FIG. 22 verses FIG. 23. As shown in FIG. 22, upon expiration, the flow braking turbulence caused by movement of the gliding sheath 210 may create a resistance such as in pursed-lip breathing, which can prop the respiratory paths open to enhance the amount of exhaled volume. Or, as shown in FIG. 23, the addition of venturi flow towards the mouth caused by movement of the gliding sheath 210 can entrain exhaled flow to enhance the overall exhaled volume. Although the gliding sheath 210 is shown to move, more or other parts can be made to move to accomplish the directed flow of this embodiment. For example, flow braking turbulence or venturi flow toward the mouth may be produced by the use of shutters, louvers, or slats.

Regardless, the flow can be directed towards the mouth or back into the lungs as desired. The flow brake for the expiratory flow of the patient can be adjusted from disturbance (pursed lips effect) or to augmentation (venturi principle). The whole catheter preferably does not have more than 4 mm outer diameter, but can be very versatile. This embodiment, like the other embodiments of the invention, can also be used to apply vibratory flow to the respiratory paths to improve mucus clearance.

The system in accordance with the principles of the invention can be implantable. In one embodiment, the system including the jet catheter and system sensors can be implanted inside the body. Although it is possible to implant the pump, it is contemplated that tubing attached to the pump can be connected to a connector exposed from the body. The pump tubing can be attached to the connector in a conventional manner so that the oxygen-bearing gas flows through the implanted jet catheters into the patient in accordance with the principles of the invention. The system can be tailored to the needs of the patient. The jet pressure and timing and duration of the pulses can be monitored and controlled and adjusted as necessary based on the patient's respiratory condition and general status. As shown in FIG. 1, the catheter can extend along the outside of the body. Alternatively, the catheter could be implanted inside the patient's body. For example, the catheter could have one exposed end for connection with the pump and some or all of the remainder of the catheter could be implanted inside the patient and/or under the skin of the patient. The output end of the catheter could, for example, be exposed for connection to the tracheal prosthesis or positioned in the nose or mouth. Furthermore, the portion of the catheter disposed in the patient can be treated. For example, it can be treated with an antibacterial, a drug, a lubricious coating, a treatment to prevent mucous formation, or otherwise.

Figure 24:
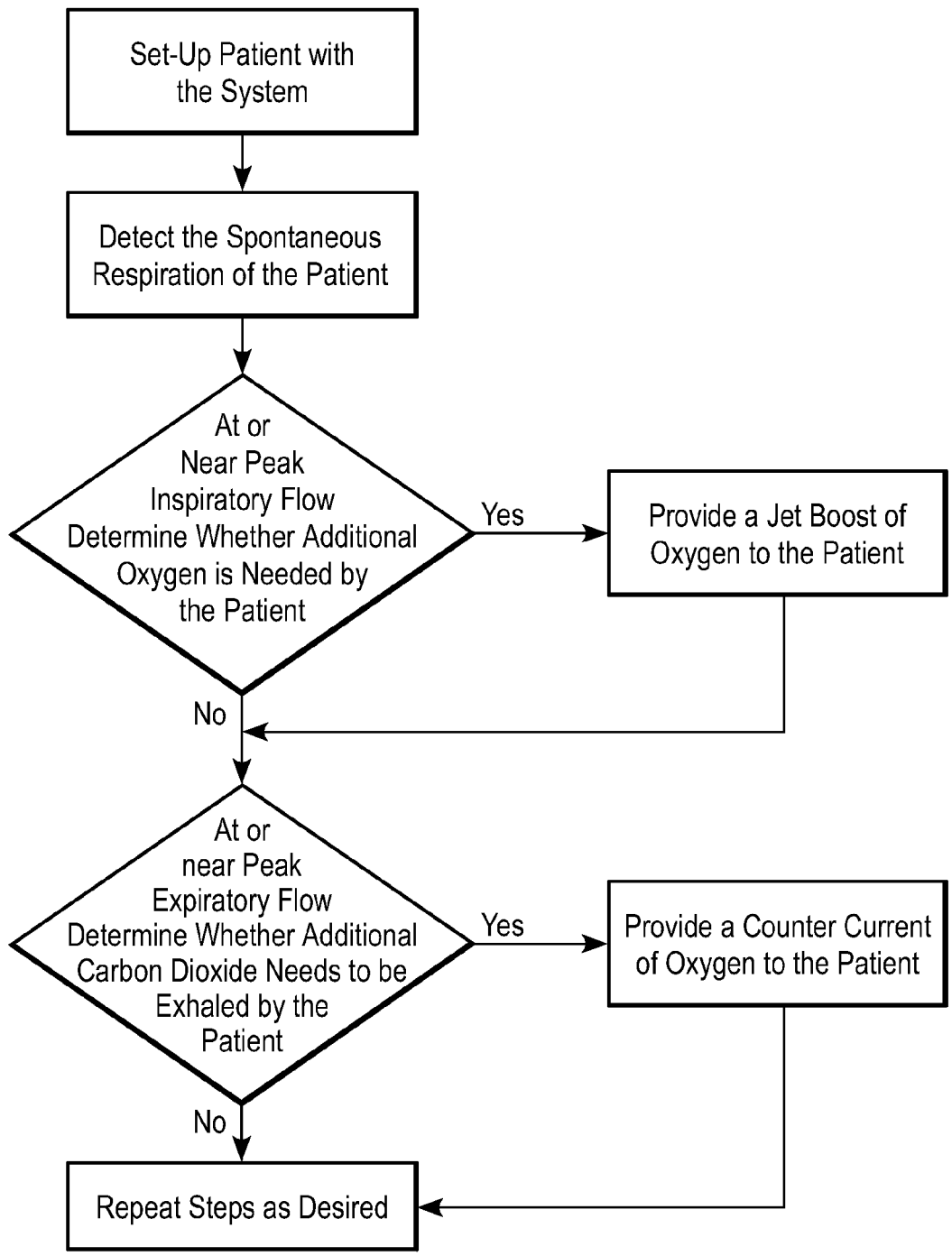
FIG. 24 is a flow diagram illustrating the operation of an embodiment of the invention.

FIG. 24 is a flow diagram illustrating an embodiment of a method of the invention. In accordance with this embodiment of the invention, the patient is provided with the system in accordance with the invention. The system is used to detect the spontaneous respiration of the patient. At or near the peak of inspiration flow, the system determines whether additional oxygen is needed by the patient. If yes, the system provides a jet boost of oxygen to the patient. Then at or near the peak of expiration flow, the system determines whether more carbon dioxide must be exhaled by the patient. If more must be exhaled, then the system provides a counter current of oxygen to the patient. The process is repeated as needed. The advantage of this embodiment is to allow the therapy to match the needs of the patient. Other ventilator systems tend to apply a predetermined therapy regardless of the changing condition of the patient, until a clinician changes a setting on the ventilator. Other ventilator systems are therapeutically suboptimal for a wide range of patient situations, often leading to over treatment, making the patient too dependent on artificial ventilation, or leading to under treatment, and thus worsening the patient's clinical condition. Therefore, in accordance with this invention the ventilator will adjust an output to the patient based on the patient's need. The ventilator can make a determination by using patient information already obtained by the sensors, such as breath rate, depth of respiration, length of inspiration or exhalation, agitation, or gas concentration levels. For example, if a patient is exercising and an unusually low exhalation flow rate is detected by the sensors, indicating that airways are collapsing too much during exhalation, then, exhalation counter flow could be switched on or increased to prop the airways open and enhance exhaled flow. Or, for example, if the patient's breathing becomes unusually fast as measured by the breath sensors, indicating the patient is compensating for shortness of breath, the inspiratory augmentation pulse could be switched on or increased to relieve the patient's dyspnea. Or as another example, gas composition sensors detecting $CO_2$, and $O_2$ levels in the airway can determine if the therapy is adequate and increase or lower the therapy as needed.

As mentioned above, the principles of the invention can be used in treating and/or assisting in the treatment of a variety of breathing disorders and/or breathing difficulties. In such treatments, the invention can provide an oxygen-bearing gas into any of the airways of the patient. In one such embodiment, instead of directing the oxygen-bearing gas into the lungs, the oxygen-bearing gas can be directed into the upper airways, including, for example, using a catheter and, more particularly, a tracheal or coated catheter.

In one embodiment, an oxygen-bearing gas can be directed into the upper airways to treat or assist in the treatment of sleep apnea. Sleep apnea is a serious sleep disorder that occurs when a person's breathing is interrupted repeatedly during their sleep. People with untreated sleep apnea stop breathing repeatedly during their sleep, sometimes hundreds of times during the night. One type of sleep apnea can be referred to as obstructive sleep apnea (OSA). OSA is caused by a blockage of the airway, usually when the soft tissue in the rear of the throat collapses during sleep. Currently, sleep apnea can be treated by continuous positive airway pressure (CPAP) treatment in which a patient wears a mask over the nose and/or mouth. An air blower forces air through the upper airway. The air pressure is adjusted so that it is just enough to prevent the upper airway tissue from collapsing during sleep. The pressure is constant and continuous, and the flow rate is sometimes adjusted by bilevel positive airways pressure (Bi-PAP) machines, depending on need. CPAP can prevent airway closure while in use, but apnea episodes return when CPAP is stopped or it is used improperly. The use of the nasal mask and oral delivery of gas/oxygen/ambient air is cumbersome and inhibits the patient. In contrast, in accordance with the principles of the invention, the oxygen-bearing gas can be provided to the patient by way of a catheter, including a tracheal catheter. The oxygen-bearing gas can be provided to the patient based upon the breathing monitored by sensors in accordance with the invention. This includes sensors placed in the upper airway tissues that sense tissue movement or collapse. These sensors could communicate to the pump via wireless or hard wire. The sensors can detect the breathing cycles and based upon that information the oxygen flow and volume can be controlled. The oxygen-bearing gas can be provided continuously, intermittently, or pulsed as needed. Alternatively, as discussed above, the oxygen-bearing gas can be provided in a jet flow. Further, the portable respiration device can be programmed such that a continuous flow of oxygen-bearing gas is delivered and a jet boost is activated only if necessary. As a result, the oxygen can be tailored to the patient's needs.

The invention can be used to treat any kind of disease where alveolar ventilation and oxygen uptake are impaired. This includes chronic obstructive airway pulmonary diseases including lung emphysema, as well as restrictive diseases such as pulmonary fibrosis, sarcoidosis, pleural adhesions, chest-wall diseases, neuromuscular diseases, and phrenic nerve paralysis. Basically, whenever a patient has a problem breathing deeply enough, the invention can be helpful.

In contrast to the present invention, typical invasive ventilation is provided all the time, but a patient cannot exercise at all (walk, carry something, etc.). The patient has a tube in the throat and is fixed to a bed (usually in intensive care). Non-invasive ventilation with a mask is sometimes provided in order to help the patient's weak breathing muscles recover. For example, if the patient is ventilated overnight, the diaphragm and auxiliary muscles can rest, and the patient can perform better at daytime. However, whenever the patient would need help most (during exercise), the patient has to breathe on their own. With the minimally invasive or percutaneous ventilation and the synchronized jet from the system in accordance with the invention, support is given when needed (e.g., during exercise).

Although the foregoing description is directed to the preferred embodiments of the invention, it is noted that other variations and modifications will be apparent to those skilled in the art, and may be made departing from the spirit or scope of the invention. Moreover, features described in connection with one embodiment of the invention may be used in conjunction with other embodiments, even if not explicitly stated above. The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes, which come within the meaning and range of equivalency of the claims, are to be embraced within their scope.

What is claimed is:

1. A method or supporting the respiration of a patient comprising the steps of:
   detecting the spontaneous respiration of the patient with sensors,
   identifying an end of an inhalation process of the spontaneous respiration.
   administering an additional amount of oxygen-bearing gas to the lungs through an oxygen-bearing gas delivery device into a respiratory system of the patient, and
   wherein the oxygen-bearing gas delivery device and the additional amount of oxygen-bearing gas allows the patient to speak unhindered.

2. The method of claim 1, wherein the amount of oxygen-bearing gas is sufficient to treat sleep apnea, COPD, emphysema, pulmonary fibrosis, sarcoidosis, pleural adhesions, chest-wall diseases, neuromuscular diseases, or phrenic nerve paralysis.

3. The method of claim 1, wherein the amount of oxygen-bearing gas is sufficient to prevent the patient's airway from collapsing.

4. The method of claim 1, wherein the sensors include thennistors, respihands, respitrace, or transthoraeieal electrical impedance measuring devices.

5. The method of claim 1, wherein the sensors are disposed at different locations.

6. The method of claim 5, further comprising dampening a signal response of a sensor relative to a signal response of an additional sensor, and comparing the signal response of the sensor and the signal response of the additional sensor for correcting signal drift transient signals and artifacts.

7. The method of claim 1, wherein inspiration and exhalation are determined with a bridge circuit and a differentiator, 8. The method of chum 7, wherein inspiration is determined at a minimum absolute temperature and a differentiated signal of zero.

9. The method of claim 1, wherein the oxygen-bearing gas delivery device comprises a tracheal prosthesis.

10. The method of claim 9, further comprising the step of securing the tracheal prosthesis in a trachea.

11. The method of claim 9, wherein the tracheal prosthesis has a circular or semicircular cross-section.

12. The method of claim 9, wherein the tracheal prosthesis further comprises a coupling adapted to receive a catheter.

13. The method of claim 1, wherein the oxygen-bearing gas is administered by jet flow.

14. The method of claim 13, wherein the oxygen-bearing gas is administered at a speed of approximately 100 m/s to 300 m/s.

15. The method of claim 14, wherein the oxygen-bearing gas is administered at a speed of approximately 200 m/s to 300 m/s.

16. The method of claim 15, wherein the oxygen-bearing gas is administered at a speed of approximately 250 m/s to 300 m/s.

17. The method of claim 1, wherein the oxygen-bearing gas delivery device comprises a catheter.

18. The method of claim 17, wherein the catheter comprises an outer lumen and an inner lumen.

19. The method of claim 17, wherein a flow of the oxygen-bearing gas is directed substantially down the center of a trachea.

20. The method of claim 1, wherein the oxygen-bearing gas is administered only on inspiration.

21. The method of claim 1, wherein the oxygen-bearing gas is administered only on expiration.

22. The method of claim 1, wherein the oxygen-bearing gas is administered during both inhalation and exhalation.

23. The method of claim 22, wherein the additional amount of oxygen-bearing gas causes flow braking turbulence or the addition of venture flow.

24. The method of claim 1, wherein information from the sensors can be communicated to a healthcare provider or hospital for monitoring.

25. A method for supporting the respiration of a patient Comprising the steps:
   detecting the spontaneous respiration of the patient with sensors,
   administering an additional amount of oxygen-bearing gas through an oxygen-bearing gas delivery device into is respiratory system of the patient, wherein the oxygen-bearing gas increases the depth of the patent's ventilation and/or reduces the patient's work of breathing, and
   wherein the oxygen-bearing gas delivery device does ma inhibit the patient from breathing freely from ambient air.

26. The method of claim 25, wherin the amount of oxygen-bearing gas is sufficient to treat sleep apnea, COPD, emphysema, pulmonary fibrosis, sarcoidosis, plaurai adhesions, chest-wall diseases, neuromusco diseases, or phrenic nerve paralysis.

27. The method of claim 25, wherein the amount of oxygen-bearing gas is sufficient to prevent the patients airway from collapsing.

28. The method of claim 25, wherein the sensors include thermistors, respibands, respitrace, or transthoracical electrical impedance measuring devices.

29. The method of claim 25, wherein the sensors are disposed at different locations.

30. The method of claim 29, further comprising dampening a signal response of a sensor relative to a signal response of an additional sensor, and comparing the signal response of the sensor and the signal response of the additional sensor for correcting signal drift, transient signals and artifacts.

31. The method of claim 25, wherein the oxygen-bearing gas selectively supplements the patient's inspiration of ambient air.

32. The method of claim 31, wherein the increased depth of the patient's ventilation and/or reduction in the patient's work of breathing is facilitated by the oxygen-bearing gas delivery device.

33. The method of claim 1, wherein the oxygen-bearing gas delivery device comprises a tracheal prosthesis.

34. The method of claim 33, further comprising the step of securing the tracheal prosthesis in a trachea.

35. The Method of claim 33, wherein the tracheal prosthesis has a circular or semicircular cross-section.

36. method of claim 33, wherein the tracheal prosthesis further comprises a coupling adapted to receive a catheter.

37. The method of claim 25, wherein the oxygen-bearing gas is administered by jet flow.

38. The method of claim 37, wherein the oxygen-bearing gas is administered at to speed of approximately 100 m/s to 300 m/s.

39. The method of claim 25, wherein the oxygen-bearing gas delivery device comprises a catheter.

40. The method of claim 39, wherein the catheter comprises an outer lumen and an inner lumen.

41. The method of claim 39, wherein a flow of the oxygen-bearing gas is directed substantially down the center of a trachea.

42. The method of claim 25, wherein the oxygen-bearing, gas is administered only on inspiration, 43. The method of claim 25 wherein the oxygen-bearing, gas is administered only on expiration.

44. The method of claim 25, wherein the oxygen-bearing gas is administered during both inhalation and exhalation.

45. The method of claim 44, wherein the additional amount of Oxygen-bearing gas causes flow braking turbulence or the addition of venturi flow.

46. The method of claim 25, wherein information from the sensors can be communicated to a healthcare provider or hospital for monitoring.

47. A method for supporting the respiration of a patient comprising the steps of:
   detecting the spontaneous respiration of the patient with sensors,
   administering an additional amount of oxygen-bearing as through an oxygen-bearing gas delivery device into a respiratory system of the patient, wherein the oxygen-bearing gas increases the depth of the patient's ventilation and/or reduces the patient's work of breathing, and
   wherein the oxygen-bearing gas delivery device and the additional amount of oxygen-bearing gas allows the patient to speak unhindered.

48. The method of claim 47, further comprising dampening a signs response of a sensor relative to a signal response of an additional sensor, and comparing the signal response of the sensor and the signal response of the additional sensor for correcting signal drift, transient signals and artifacts.

49. The method of claim 47, wherein the oxygen-bearing gas is administered only on inspiration.

50. The method of claim 47, wherein the oxygen-bearing gas is administered only on expiration.

51. The method of claim 47, wherein the oxygen-bearing gas is administered during both inhalation and exhalation.

52. A method for supporting the respiration of a patient Comprising:
   operatively interfacing an oxygen-bearing gas delivery device to the respiratory system of the patient,
   fluidly connecting to the oxygen-bearing gas delivery device to an oxygen-bearing gas source,
   operatively interfacing at least one sensor to the patient,
   operatively interfacing a control unit to the sensor and the oxygen-bearing gas source, and
   selectively activating the oxygen-bearing gas source based on a signal provided to the control unit connected by the sensor,
   wherein an oxygen-hearing gas provided to the patient by the oxygen-bearing gas source increases the depth of the padent's ventilation and/or reduces the patient's work of breathing, and wherein the oxygen-bearing gas delivery device does not inhibit the patient from breathing freely from ambient air.

53. The method of claim 52, further comprising the step of detecting the spontaneous respiration of the patient through the use of the sensor.

54. In The method of claim 52, wherein the step of operatively interfacing at least one sensor to the patient comprises operatively interfacing at least first and second sensors to the patient.

55. The method of claim 54, wherein the step of operatively interfacing at least first and second sensors to the patient sensors further comprises disposing the first and second sensors at different locations.

56. The method of claim 55, further comprising the step of dampening a signal response of the first sensor to a signal response of the second sensor, and comparing the signal response of the first sensor to the signal response of the second sensor for correcting signal drift, transient signals and artifacts.

57. The method of claim 55, further comprising step of implanting at least one of the first and second sensors into the patient's body.

58. The method of claim 52, wherein the oxygen-bearing gas selectively supplements the patient's inspiration of ambient air.

59. The method of claim 58, wherein the increased depth of the patients ventilation and/or reduction in the patient's work of breathing is facilitated by the oxygen-bearing gas delivery device.

60. A method for supporting the respiration of a patient comprising:

operatively interfacing an oxygen-bearing gas delivery device, to the respiratory system of the patient, fluidly connecting to the oxygen-bearing gas delivery device to an oxygen-bearing gas source, operatively, interfacing at least one sensor to the patient, operatively interfacing a control unit to the sensor and the oxygen-bearing gas source, and selectively activating the oxygen-bearing gas source based on a signal provided to the control unit connected by the sensor, wherein an oxygen-bearing gas provided to the patient by the oxygen-bearing gas source increases the depth of the patient's ventilation and/or reduces the patient's work of breathing, and wherein the oxygen-bearing gas delivery device allows the patient to speak unhindered.

61. The method of claim 60, wherein the step of operatively interfacing at least one sensor to the patient comprises operatively interfacing at least first and second sensors to the patient.

62. The method of claim 61, wherein the step of operatively interfacing at least first and second sensors to the patient sensors further comprises disposing the first and second sensors at different locations.

63. The method of claim 61, further comprising the step of dampening a signal response of the first sensor relative to a signal response of the second sensor, and comparing the signal response of the first sensor to the signal response of the second sensor for correcting signal drift, transient signals and artifacts.

64. The method of claim 61, further comprising the step of implanting at least one of the first and second sensors into the patients body.

* * * * *